(12) United States Patent
Mousa

(10) Patent No.: US 8,980,823 B2
(45) Date of Patent: Mar. 17, 2015

(54) FORMULATIONS OF FACTOR VIIA INHIBITORS AND UTILITY

(71) Applicant: Shaker A. Mousa, Wynantskill, NY (US)

(72) Inventor: Shaker A. Mousa, Wynantskill, NY (US)

( * ) Notice: Subject to any disclaimer, the term of this patent is extended or adjusted under 35 U.S.C. 154(b) by 0 days.

(21) Appl. No.: 13/935,665

(22) Filed: Jul. 5, 2013

(65) Prior Publication Data

US 2013/0295187 A1 Nov. 7, 2013

Related U.S. Application Data

(63) Continuation-in-part of application No. 13/414,106, filed on Mar. 7, 2012, now Pat. No. 8,481,479.

(51) Int. Cl.

| A61K 38/00 | (2006.01) |
|---|---|
| A61K 38/05 | (2006.01) |
| C07K 14/755 | (2006.01) |
| A61K 47/48 | (2006.01) |
| A61K 9/50 | (2006.01) |
| A61K 31/195 | (2006.01) |
| A61K 31/4245 | (2006.01) |
| A61K 31/437 | (2006.01) |
| C12N 9/64 | (2006.01) |
| A61K 38/48 | (2006.01) |

(52) U.S. Cl.
CPC ......... *A61K 47/48315* (2013.01); *A61K 9/5036* (2013.01); *A61K 31/195* (2013.01); *A61K 9/5031* (2013.01); *A61K 31/4245* (2013.01); *A61K 31/437* (2013.01); *C12N 9/6437* (2013.01); *A61K 47/48884* (2013.01); *A61K 38/4846* (2013.01)
USPC .......................................................... 514/1.1

(58) Field of Classification Search
None
See application file for complete search history.

(56) References Cited

U.S. PATENT DOCUMENTS

| 6,262,233 | B1 | 7/2001 | Gentz et al. |
|---|---|---|---|
| 6,358,960 | B1 | 3/2002 | Senokuchi et al. |
| 6,699,994 | B1 | 3/2004 | Babu et al. |
| 8,481,479 | B1 * | 7/2013 | Mousa ........................... 514/1.1 |
| 2007/0122440 | A1 | 5/2007 | Macosko et al. |
| 2008/0286372 | A1 | 11/2008 | Pacetti et al. |
| 2013/0158089 | A1 | 6/2013 | Loury et al. |

OTHER PUBLICATIONS

Cancado, "Sickle cell disease: looking back but towards the future," Rev. Bras. Hematol. Hemoter. 34:175-177 (2012).*
Rees et al., "Sickle cell disease," Lancet 376:2018-2031 (2010).*
Solovey et al., "Tissue factor expression by endothelial cells in sickle cell anemia," J. Clin. Invest. 101:1899-1904 (1998).*
Leavitt, "Are there more tricks in the bag for treating thrombocytopenia?," J. Clin. Invest. 120:3807-3810 (2010).*
Saini et al., "Pharmacological basis of different targets for the treatment of atherosclerosis," J. Cell. Mol. Med. 9:818-839 (2005).*
Mannucci, "Hemophilia: treatment options in the twenty-first century," J. Thromb. Haemo. 1:1349-55 (2003).*
U.S. Appl. No. 13/414,106, filed Mar. 7, 2012, First Named Inventor Shaker A. Mousa, Confirmation No. 2236.
Krishnan, R. et al., Probing the S2 site of factor VIIa to generate potent and selective inhibitors: the structure of BCX-3607 in complex with tissue factor-factor VIIa, Acta Cryst. D63:689-697, 2007.
Miura, M. et al., Potent and selective TF/FVIIa inhibitors containing a neutral P1 ligand, Bioorg. Med Chem 14:7688-7708, 2006.
Hu, H., et al., Potent 4-amino-5azaindole factor VIIa inhibitors, Bioorg. Med Chem 16:4567-4570, 2006.
International Search Report, International application No. PCT/US2014/045177, date of Mailing Oct. 31, 2014, Applicant Mousa, Shaker A., 12 pages.

* cited by examiner

Primary Examiner — Julie Ha
Assistant Examiner — Kristina M Hellman
(74) Attorney, Agent, or Firm — Schmeiser, Olsen & Watts, LLP

(57) ABSTRACT

A method for treating a subject, such as a human patient, having a vascular disorder. The treatment method administers a therapeutic effective amount of a nanoparticle or a chemical structure to the subject to treat the disorders. The nanoparticle includes a poly L-arginine polymer and a Factor VIIa inhibitor conjugated to, or encapsulated in, the poly L-arginine polymer. The chemical structure includes a Factor VIIa inhibitor that includes at least one nitric oxide (NO) donor. The disorder may be sickle cell disease; stimulated or pathological angiogenesis associated disorders, cancer, ocular angiogenesis-mediated disorders such as diabetic retinopathy and macular degeneration, coagulation and/or platelet activation-associated disorders, pulmonary hypertension, or combinations thereof.

22 Claims, 9 Drawing Sheets

FORMULATIONS OF FACTOR VIIA INHIBITORS AND UTILITY

This application is a continuation-in-part application claiming priority to Ser. No. 13/414,106, filed Mar. 7, 2012, now U.S. Pat. No. 8,481,479, issued Jul. 9, 2013.

FIELD OF THE INVENTION

The field relates to the use of novel nanoparticle formulations and chemical structures that include vasodilator Factor VIIa inhibitors to treat vascular disorders in a subject.

BACKGROUND OF THE INVENTION

Vascular endothelial-mediated disorders including sickle cell diseases, tissue ischemia, and circulatory disorders such as venous and arterial thromboembolic disorders, which represent a major medical dilemma and treatment of these disorders represents an unmet clinical need. Furthermore, excessive abnormal or pathological angiogenesis is associated with various tumor progression and metastasis, which can be blocked by Factor VIIa inhibitors. Similarly, pathological or stimulated angiogenesis is also associated with ocular disorders such as diabetic retinopathy (DR) and age-related macular degeneration (AMD), which can be reversed by our novel factor VIIa inhibitors. Additionally, other major vascular disorders with unmet clinical needs include pulmonary hypertension (PH) and a form of PH called pulmonary arterial hypertension (PAH). PH is a disorder characterized by abnormally high blood pressure in the lungs. Further, the narrowing of vasculature that occurs in many of these diseases causes the buildup of pressure and the heart must work harder in order to force blood through the pulmonary arteries. PH is an increase in blood pressure in the pulmonary artery, pulmonary vein, and/or pulmonary capillaries. PH is a very serious condition, potentially leading to shortness of breath, dizziness, fainting, decreased exercise tolerance, heart failure, pulmonary edema, and death. PH is generally characterized by a mean pulmonary artery pressure exceeding 25 mm Hg (3300 Pa) at rest or 30 mm Hg (4000 Pa) with exercise and the World Health Organization (WHO) has subdivided PH into five different groups:

WHO Group I—Pulmonary arterial hypertension (PAH)
  Idiopathic (IPAH)
  Familial (FPAH)
  Associated with other diseases (APAH): collagen vascular disease (e.g. scleroderma), congenital shunts between the systemic and pulmonary circulation, portal hypertension, HIV infection, drugs, toxins, or other diseases or disorders
  Associated with venous or capillary disease
WHO Group II—Pulmonary hypertension associated with left heart disease
  Atrial or ventricular disease
  Valvular disease (e.g. mitral stenosis)
WHO Group III—Pulmonary hypertension associated with lung diseases and/or hypoxemia
  Chronic obstructive pulmonary disease (COPD), interstitial lung disease (ILD)
  Sleep-disordered breathing, alveolar hypoventilation
  Chronic exposure to high altitude
  Developmental lung abnormalities
WHO Group IV—Pulmonary hypertension due to chronic thrombotic and/or embolic disease
  Pulmonary embolism in the proximal or distal pulmonary arteries
  Embolization of other matter, such as tumor cells or parasites WHO Group V—Miscellaneous PH involves the vasoconstriction or tightening of blood vessels connected to and within the lungs. This tightening makes it harder for the heart to pump blood through the lungs, much as it is harder to make water flow through a narrower pipe as opposed to a wider pipe. Over time, the blood vessels affected by this vasoconstriction become both stiffer and thicker, in a process known as fibrosis. This fibrosis further increases the blood pressure within the lungs and impairs blood flow. In addition, the increased workload of the heart causes thickening and enlargement of the right ventricle, making the heart less able to pump blood through the lungs, causing right heart failure. As blood flowing through the lungs decreases, the left side of the heart receives less blood and this blood may also carry less oxygen than normal. Therefore it becomes harder and harder for the left side of the heart to pump to supply sufficient oxygen to the rest of the body, especially during physical activity.

In pulmonary venous hypertension (WHO Group II) there is not necessarily any obstruction to blood flow in the lungs. Instead, the left heart fails to pump blood efficiently out of the heart into the body, leading to pooling of blood in veins leading from the lungs to the left heart (congestive heart failure). This causes pulmonary edema and pleural effusions. The fluid build-up and damage to the lungs may also lead to hypoxia and consequent vasoconstriction of the pulmonary arteries, so that the pathology may come to resemble that of Group I or III.

In hypoxic pulmonary hypertension (WHO Group III), the low levels of oxygen may cause vasoconstriction or tightening of pulmonary arteries. This leads to a similar pathophysiology as PAH.

In chronic thromboembolic pulmonary hypertension (WHO Group IV), the blood vessels are blocked or narrowed with blood clots. Again, this leads to a similar pathophysiology as pulmonary arterial hypertension.

The pathogenesis of PH involves a complex and multifactorial process. Endothelial dysfunction seems to play an integral role in mediating the structural changes in the pulmonary vasculature that occur as a result of PH. These dysfunctions include disordered endothelial cell proliferation and concurrent neoangiogenesis. When this angiogenesis is exuberant, it results in the formation of glomeruloid structures known as plexiform lesions. In addition, a decrease in the vasodilators nitric oxide (NO) and prostacyclin, along with an increase in vasoconstrictors such as endothelin-1 (ET-1), serotonin, and thromboxane, have been observed in patients with PH. Because most of these mediators affect the growth of the smooth muscle cells, an alteration in their production or expression may facilitate the development of pulmonary vascular hypertrophy and the structural remodeling of the vasculature that is characteristic of PH. It is conceivable that the beneficial effects of many of the treatments currently available for PH, such as the use of prostacyclin, NO, and ET-1 antagonists, result at least in part from restoring the balance between these mediators.

In addition to the potential consequences of an imbalance in the endothelial production of various mediators, injury to the endothelium caused by PH may expose the underlying vascular tissue to diverse blood-borne factors that may further promote pathological changes. Endothelial dysfunction may also have adverse consequences on pulmonary vascular hemostasis by altering the production of anticoagulant factors. Recent reports of genetic mutations in the endothelial cells of patients with PH further underscore the role of these cells in the disease pathogenesis.

Available evidence suggests that NO is at least partially responsible for resting pulmonary vasorelaxation. Endothelial NO synthetase (eNOS) catalyzes the conversion of L-arginine to citrulline, producing NO. In addition, NO activates guanylate cyclase and increases cyclic guanine mono phosphate (cGMP) levels in smooth muscle cells, causing vasodilatation. The specific role of eNOS in pulmonary vascular tone regulation is best demonstrated in animal models. Overproduction of eNOS in transgenic mice prevents hypoxia-induced PH (3, 4).

Tissue factor (TF) is a transmembrane glycoprotein that initiates the coagulation cascade when complexed with factor VIIa and may also participate in angiogenesis and inflammation. In situ thrombosis occurs in severe PH, and there are several reports linking platelet activation to the etiology of severe disease. TF has also been shown to regulate intimal hyperplasia in response to systemic arterial injury. The TF and factor VIIa complex (TF/VIIa) might play a key role in the disordered angiogenesis and intimal hyperplasia seen in PH. Lung sections from PH lung immunostained with an antibody to TF showed that alveolar epithelium and bronchi stained abundantly for TF. TF was not seen in normal pulmonary arterial vascular cells. In contrast, animals with PH had modest TF staining in diseased vessels and more pronounced TF staining in the plexiform-like lesions. The disordered angiogenesis and neointimal lesions of severe human disease might be mediated via the TF/VIIa pathway and this approach may be a better model for the vascular pathology of moderate to severe human PH. Over-expression of Tissue Factor Pathway Inhibitor (TFPI) in pulmonary vascular beds results in improved hemodynamic performance and reduced pulmonary vascular remodeling in a murine model of hypoxia-induced PH. This improvement is in part due to autocrine and paracrine effects of TFPI overexpression.

For WHO Group II pulmonary hypertension, the first approach is to optimize left ventricular function by the use of diuretics, beta blockers, Angiotensin Converting Enzyme (ACE) inhibitors, etc., or to repair/replace the mitral valve or aortic valve. Where there is PAH, treatment is more challenging, and may include lifestyle changes. Treatment of PAH with digoxin, diuretics, oral anticoagulants, and oxygen therapy are conventional, but not highly effective. Newer drugs targeting the pulmonary arteries include endothelin receptor antagonists (e.g., bosentan, sitaxentan, ambrisentan), phosphodiesterase type 5 inhibitors (e.g., sildenafil, tadalafil), prostacyclin derivatives (e.g., epoprostenol, treprostenil, iloprost, beroprost), and soluble guanylate cyclase (sGC) activators (e.g., cinaciguat and riociguat). One surgical approach to PAH treatment is atrial septostomy to create a communication between the right and left atria, thereby relieving pressure on the right side of the heart, but at the cost of lower oxygen levels in blood (hypoxia). Other surgical approaches include lung transplantation and pulmonary thromboendarterectomy (PTE) to remove large clots along with the lining of the pulmonary artery.

There is thus an unmet need for improved treatments for PH, particularly PAH, for cardiac insufficiency due to partial or complete blockage of coronary arteries and/or damage due to myocardial infarction (e.g., acute or congestive heart failure and acute myocardial infarction). There is moreover a need for a means of delivering factor VIIa inhibitors on a sustained basis to treat such conditions.

SUMMARY OF THE INVENTION

The present invention provides a method of treating a subject having a vascular disorder, said method comprising administering a therapeutic effective amount of a nanoparticle or chemical structure of the present invention to the subject to treat the vascular disorder. The nanoparticle comprises a poly L-arginine polymer and a Factor VIIa inhibitor conjugated to or encapsulated in the poly L-arginine polymer. The chemical structure includes a Factor VIIa inhibitor that includes at least one nitric oxide (NO) donor. The disorder may be sickle cell disease; stimulated or pathological angiogenesis associated disorders, ocular angiogenesis-mediated disorders, coagulation and/or platelet activation disorders, pulmonary hypertension, or combinations thereof.

DETAILED DESCRIPTION OF THE INVENTION

Figure 1A:
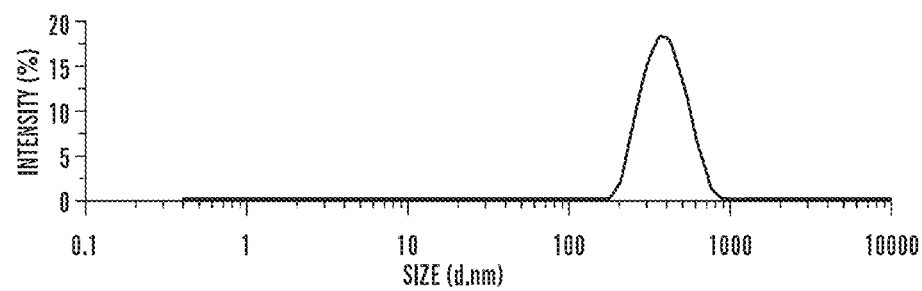
FIGS. 1A and 1B depict plots of the intensity of scattered nanoparticles versus (i) particle diameter size in nanometers (FIG. 1A) and (ii) Zeta potential due to surface charge (FIG. 1B), for Factor VIIa inhibitor (or Factor VIIa inhibitor-NO) encapsulated in poly L-arginine nanoparticles, in accordance with embodiments of the present invention.

The examples and drawings provided in the detailed description are merely examples, which should not be used to limit the scope of the claims in any claim construction or interpretation.

Pulmonary hypertension (PH) and pulmonary arterial hypertension (PAH) are commonly recognized complication of chronic respiratory disease. Enhanced vasoconstriction, pulmonary vascular remodeling and in situ thrombosis contribute to the increased pulmonary vascular resistance observed in PH associated with hypoxic lung disease. The tissue factor/factor VIIa pathway regulates fibrin deposition in response to acute and chronic vascular injury, which can be modulated by factor VIIa inhibitors. Having NO donor within the structure of Factor VIIa inhibitor or formulating Factor VIIa inhibitor in a poly L-arginine nanoparticle (i.e., a nanoparticle comprising a poly L-arginine polymer) according to the present invention provides dual function in attacking this complex disorder as well as other vascular disorders including sickle cell, peripheral artery diseases, critical limb ischemia, acute coronary syndrome, stroke, and other vasoconstrictor or pro-thrombotic-mediated disorders.

Factor VIIa inhibitors-NO (i.e., a chemical structure, comprising a Factor VIIa inhibitor that includes at least one nitric oxide (NO) donor) donor and its nanoformulations dilate the cardiac arteries and enhance cardiac function. Factor VIIa inhibitors-NO donor are therefore useful for treating acute myocardial infarction and for treating heart failure resulting from myocardial infarction. In one embodiment, the Factor VIIa inhibitors or Factor VIIa inhibitors-NO donor are encapsulated or covalently bonded to poly L-arginine (PLA) or the above-modified poly L-arginine nanoparticles can be used in a drug-eluting stent (e.g., for subjects having had or at risk of acute myocardial infarction) such as for insertion in the coronary artery. A subject is defined to be a human being or a mammal. In one embodiment, the subject is a human patient.

The present invention provides inhalable (for example, aerosol therapy using micro spray techniques), oral, or injectable Factor VIIa inhibitors containing NO donor nanoparticle formulations, wherein the Factor VIIa inhibitor containing NO donor is encapsulated into biodegradable polymers that release L-arginine that is converted to Nitric Oxide for vasodilatation.

In one embodiment, a nanoparticle of the present invention comprises a poly L-arginine polymer and a Factor VIIa inhibitor, wherein the Factor VIIa inhibitor either includes or does not include a nitric oxide (NO) donor.

In one embodiment, the polymer comprises poly-L-arginine.

In one embodiment, the polymer comprises poly-L-arginine bonded to fatty acids.

In one embodiment, the polymer comprises poly-L-arginine cross-linked with gluteraldehyde.

In one embodiment, the polymer comprises poly-L-arginine linked to bile acids.

In one embodiment, the polymer comprises poly-L-arginine linked to hyaluronic acid.

In one embodiment, the polymer comprises poly-L-arginine linked to low molecular to ultra low molecular weight chitosan.

In one embodiment, the polymer comprises poly-L-arginine linked to other amino acids such as tyrosine, L-Lysine, etc.

In one embodiment, the polymer comprises poly-L-arginine linked to PLGA. Where in PLGA could be poly (D,L-lactide-co-glycolide) (PLGA) and poly (vinyl sulfonate-co-vinyl alcohol).

In one embodiment, the polymer comprising poly-L-arginine linked to the above moieties is conjugated to a site directed probe that recognizes pulmonary tissues and compromised vascular tissues for homing the active compound into lung tissue and deep penetration into pulmonary tissues.

In one embodiment, the nanoparticles have an average diameter in a range of 50-1000 nm; e.g., 100-500 nm or 50-250 nm.

In one embodiment, the nanoparticles have a zeta potential of 0 to 100 mV (e.g., 0 to +50 mV).

In one embodiment, the Factor VIIa inhibitors are conjugated to (e.g., by being covalently linked to) the poly L-arginine polymer.

In one embodiment, the Factor VIIa inhibitors are encapsulated in the poly-L-arginine polymer and not covalently linked to the poly L-arginine polymer.

In one embodiment, the formed nanoparticles are coated with polyethylene glycol (PEG), bile salt, lipid, or other permeation enhancers/stabilizers.

In one embodiment, the formed poly-L-arginine nanoparticles are encapsulated in liposomes with sizes in the 1-100 micrometer ranges (e.g., 10-20 micrometers).

In one embodiment, the present invention provides a nanoparticle that comprises a poly L-arginine polymer and a Factor VIIa inhibitor conjugated to or encapsulated in the L-arginine polymer, wherein the Factor VIIa inhibitor includes a nitric oxide (NO) donor. In one example, the Factor VIIa inhibitor is conjugated to the poly L-arginine polymer by being covalently bonded to the poly L-arginine polymer. In one example, the Factor VIIa inhibitor is encapsulated in the poly L-arginine polymer and not covalently bonded to the poly L-arginine polymer. In one example, the poly L-arginine polymer is cross-linked with at least one substance selected from the group consisting of chitosan, lactic-co-glycolic acid (PLGA), fatty acids, bile acids, amino acids, and combinations thereof.

In one embodiment, the present invention provides a nanoparticle that comprises a poly L-arginine polymer and a Factor VIIa inhibitor, wherein the Factor VIIa inhibitor does not include a nitric oxide (NO) donor.

In one embodiment, the present invention provides a chemical structure, wherein the chemical structure comprises a Factor VIIa inhibitor that includes at least one nitric oxide (NO) donor.

In one embodiment, the present invention provides a treatment method of treating a subject having a disorder, wherein the treatment method comprises administering a therapeutic effective amount of a nanoparticle or chemical structure of the present invention to the subject to treat the disorder, and wherein the disorder is a vascular disorder, cardiac insufficiency, a neurological disorder, or combinations thereof. In one example, the vascular disorder comprises pulmonary hypertension (e.g., pulmonary arterial hypertension).

In one embodiment, the Factor VIIa inhibitor nanoparticle formulation may be made from one or more Factor VIIa inhibitors and at least one component of the following components:

Poly L-Arginine

[Chemical structure of Chitosan]

[Chemical structure of PLGA]

[Chemical structure of PVA (stabilizer)]

[Chemical structure of Polyethylene glycol]

Liposome

In one example, the components in the nanoparticle formulation are as described in Table 1 infra.

TABLE 1

Components of the Nanoparticle Formulation

| Components of the Nanoparticle Formulation | Approximate Amount (weight percent) in the Nanoparticle Formulation | Role in the Nanoparticle Formulation |
|---|---|---|
| L-arginine | 50-70%, e.g. 60% | Component of the nanoparticle |
| Fatty acids, bile acids, amino acids, PLGA, Chitosan (each cross-linked with L-arginine) | 10-20%, e.g. 15% | Component of the nanoparticle |
| Factor VIIa inhibitors | 20-30%, e.g. 25% | Active ingredient (e.g., non-covalently encapsulated in or covalently linked to the L-poly-arginine nanoparticles) |
| Factor VIIa inhibitors-NO Donors | 20-100% | Active ingredient stand alone (100%) or encapsulated non-covalently or chemically conjugated covalently to the L-poly-arginine nanoparticles |
| Liposome | Outer shell (1-100 uM), average 10-20 uM | Encapsulate multiple nanoparticles formed by a-c |

The fatty acids that may be cross-linked with L-arginine may be unsaturated fatty acids such as:
Oleic acid: $CH_3(CH_2)_7CH=CH(CH_2)_7COOH$
Linoleic acid: $CH_3(CH_2)_4CH=CHCH_2CH=CH(CH_2)_7COOH$
α-Linoeic acid: $CH_3CH_2CH=CHCH_2CH=CHCH_2CH=CH(CH_2)_7COOH$
Docosahexaeonic acid: $CH_3CH_2CH=CHCH_2CH=CHCH_2CH=CHCH_2CH=CHCH_2CH=CHCH_2CH=CH(CH_2)_2COOH$ The fatty acids that may be cross-linked with L-arginine may be saturated fatty acids such as the saturated fatty acids listed in Table 2 infra.

TABLE 2

Examples of Saturated Fatty Acids

| Common Name of Saturated Fatty Acids | Chemical Structure |
|---|---|
| Caprylic acid | $CH_3(CH_2)_6COOH$ |
| Capric acid | $CH_3(CH_2)_8COOH$ |
| Lauric acid | $CH_3(CH_2)_{10}COOH$ |
| Myristic acid | $CH_3(CH_2)_{12}COOH$ |

TABLE 2-continued

Examples of Saturated Fatty Acids

| Common Name of Saturated Fatty Acids | Chemical Structure |
|---|---|
| Palmitic acid | $CH_3(CH_2)_{14}COOH$ |
| Stearic acid | $CH_3(CH_2)_{16}COOH$ |
| Arachidic acid | $CH_3(CH_2)_{18}COOH$ |
| Behenic acid | $CH_3(CH_2)_{20}COOH$ |
| Lignoceric acid | $CH_3(CH_2)_{22}COOH$ |
| Cerotic acid | $CH_3(CH_2)_{24}COOH$ |

The contents of the nanoparticles are confirmed using, for example, HPLC and LC/MS. The nanoparticle formulations may be sterilized using conventional means; e.g., filtration, gamma radiation.

In one embodiment, the present invention provides a method for treating pulmonary hypertension and pulmonary arterial hypertension. The method comprises administering an effective amount of a Factor VIIa inhibitors containing NO donor-nanoparticle formulation to a subject in need thereof, wherein the Factor VIIa inhibitors NO donor-nanoparticle comprises a biodegradable polymer.

In one embodiment, the invention provides a method for treating cardiac insufficiency; e.g., heart failure, angina, or acute myocardial infarction. The method comprises administering an effective amount of Factor VIIa inhibitors-NO donor nanoparticle formulation to a subject in need thereof, wherein the Factor VIIa inhibitors-NO donor nanoparticle comprises a biodegradable polymer.

In one example of the foregoing methods, the administered nanoparticle comprises Poly L-arginine nanoparticles encapsulating Factor VIIa inhibitors or Factor VIIa inhibitor-NO.

In an example, the Factor VIIa inhibitors or Factor VIIa inhibitors-NO donor nanoparticle administered comprises Poly L-arginine nanoparticles encapsulating Factor VIIa inhibitors or Factor VIIa inhibitors-NO donor with gluteraldehyde as a cross linker. Other cross-linkers may be used. In another example, the Factor VIIa inhibitors or Factor VIIa inhibitors-NO donor nanoparticle administered comprises Poly L-arginine-PLGA nanoparticles encapsulating Factor VIIa inhibitors. Such examples of Factor VIIa inhibitors or Factor VIIa inhibitors-NO donor nanoparticles may utilize a process that includes gelation/conjugation of preformed biodegradable polymers.

In an example, the Factor VIIa inhibitors or Factor VIIa inhibitors-NO donor nanoparticle administered includes Poly L-arginine-fatty acid conjugated nanoparticles immobilizing Factor VIIa inhibitors or Factor VIIa inhibitors-NO donor. Alternatively, the Factor VIIa inhibitors or Factor VIIa inhibitors-NO donor nanoparticles administered comprises Poly L-arginine nanoparticles immobilizing or covalently linking Factor VIIa inhibitors.

In an example, the factor VIIa inhibitor-nanoparticle formulation with poly L-arginine and its cross-linked moieties is encapsulated or conjugated to Poly L-arginine placed into liposomes and is administered by inhalation, oral, or injectable.

In one embodiment, administration is by a pump activated by a signal, which releases the nanoparticles into the bloodstream. In one embodiment the signal is generated when pulmonary arterial pressure rises above a given level; e.g., greater than 30, for example, greater than 40 mmHg, as measured by an electronic pressure transducer linked to a cannula in the pulmonary artery.

In one embodiment, the present invention employs a drug eluting stent, wherein the drug eluted comprises Factor VIIa inhibitors or Factor VIIa inhibitors-NO donor nanoparticles.

In one embodiment, the present invention employs inhalation delivery systems using liposome, which releases Factor VIIa inhibitors or Factor VIIa inhibitors-NO donor nanoparticles into the pulmonary tissues.

In one embodiment, the present invention employs oral delivery systems which release Factor VIIa inhibitors or Factor VIIa inhibitors-NO donor nanoparticles into the bloodstream, with site directed delivery to pulmonary tissues.

In one embodiment, the present invention employs injectable delivery systems which release Factor VIIa inhibitors or Factor VIIa inhibitors-NO donor nanoparticles into the bloodstream, with site directed delivery to pulmonary tissues.

The Factor VIIa inhibitors-NO donor and its nanoparticles of the present invention may be administered in conjunction with, or adjunctive to, the normal standard of care for pulmonary hypertension or cardiac insufficiency or other cardiovascular or neurological disorders, for example in conjunction with one or more of the followings:
(i) one or more drugs selected from the group consisting of endothelin receptor antagonists (e.g., bosentan, sitaxentan, ambrisentan), phosphodiesterase type 5 inhibitors (e.g., sildenafil, tadalafil), prostacyclin derivatives (e.g., epoprostenol, treprostenil, iloprost, beroprost), and/or soluble guanylate cyclase (sGC) activators (e.g., cinaciguat and riociguat);
(ii) diuretics (e.g., hydrochlorothiazide);
(iii) antiplatelets (e.g., aspirin);
(iv) calcium channel blockers (e.g., amlodipine);
(v) beta-blockers (e.g. metoprolol);
(vi) ACE inhibitors (e.g. captopril, enalapril, lisinopril);
(vii) inhaled beta-agonists, corticosteroids, and/or anti-asthma drugs,
(viii) angiotensin Receptor Blockers (e.g., Losartan).

Various methods of synthesizing Factor VIIa inhibitors or Factor VIIa inhibitors-NO donor nanoparticles are provided. For example, a single emulsion process may produce chitosan-PLGA nanoparticles encapsulating Factor VIIa inhibitors or Factor VIIa inhibitors-NO donor. In yet another example, a process involving gelation/conjugation of preformed biodegradable polymers produces: (1) Poly L-arginine nanoparticles encapsulating Factor VIIa inhibitors or Factor VIIa inhibitors-NO donor with and without glutaraldehyde as a cross-linker; (2) Poly L-arginine-PLGA; (3) Poly L-arginine-fatty acid conjugated; or (4) Poly L-arginine bile acid conjugated nanoparticles encapsulating Factor VIIa inhibitors or Factor VIIa inhibitors-NO donor. Other cross-linkers may be used.

In an example, a process involving chemical bonding of Factor VIIa inhibitors or Factor VIIa inhibitors-NO donor on the surface of Poly L-arginine nanoparticles and its various conjugated forms as described above.

Administration routes include, but not limited to, intravenous, intra-arterial, intra-cardiac, subcutaneous, intramuscular, oral, and/or intrapulmonary (e.g., by inhalation). The formulation may be for immediate release (e.g., via intravenous, intra-arterial, or intra-cardiac injection), or may be in the form of a sustained release depot formulation (e.g., a depot comprising a biodegradable polymer comprising the Factor VIIa inhibitors or Factor VIIa inhibitors-NO donor nanoparticles of the invention, for example for subcutaneous, inhalation or oral resulting in release of Factor VIIa inhibitors or Factor VIIa inhibitors-NO donor over a period of several hours, one day, or even longer).

Factor VIIa Inhibitors, Factor VIIa inhibitors-NO donor as used herein includes all inhibitors of the Tissue Factor/Factor VIIa complex, all inhibitors of Factor VIIa, and all inhibitors of Tissue Factor. The inhibitor may be of any composition, including small molecules, inactivated factor VII, antibody to TF/VIIa conjugated with NO donors.

Alternative combinations and variations of the examples provided will become apparent to one of ordinary skill in the art based on this disclosure of the present invention. It is not possible to provide specific examples for all of the many possible combinations and variations of the embodiments described, but such combinations and variations may be determined by one of ordinary skill in the art, based on this disclosure of the present invention, without undue experimentation and are included within the scope of the disclosed present invention Examples of Factor VIIa inhibitor (I, II, III, and IV) chemically-conjugated with group $R_1$, or both groups $R_1$ and $R_2$, are as follows:

(Factor VIIa inhibitor I in which the group $R_1$ can be located at one or more positions of positions 3, 4, 5, and 6 as single, double, or triple substitutions);

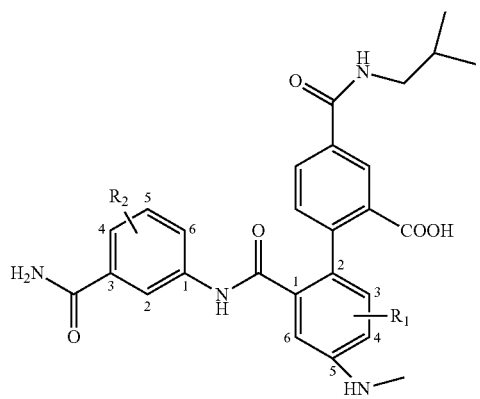

(Factor VIIa inhibitor II in which the group $R_1$ can be located at one or more positions of positions 3, 4, and 6 as single, double, or triple substitutions and in which the group $R_2$ can be located at one or more positions of positions 2, 4, 5, and 6 as single, double, or triple substitutions);

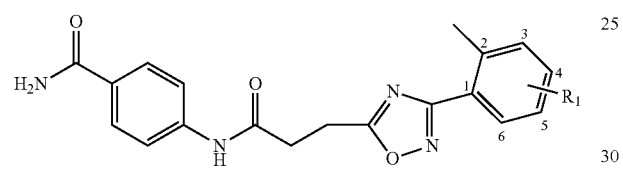

(Factor VIIa inhibitor III in which the group $R_1$ can be located at one or more positions of positions 3, 4, 5, and 6 as single, double, or triple substitutions);

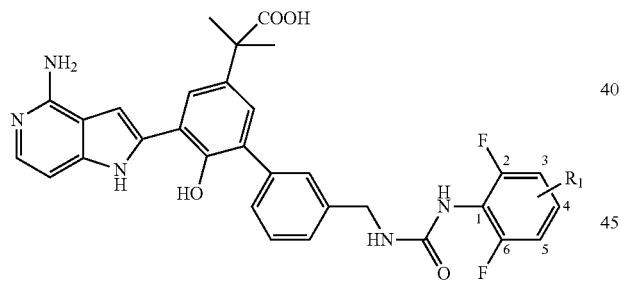

(Factor VIIa inhibitor IV in which the group $R_1$ can be located at one or more positions of positions 3, 4, and 5 as single, double, or triple substitutions).

For Factor VIIa inhibitors I, II, III, and IV, the group $R_1$ is either hydrogen (H) which is denoted as $R_{10}$ or any of the following NO donors:

| | |
|---|---|
| O=N—S— | ($R_{11}$); |
| —ONO$_2$ | ($R_{12}$); |
| —CH$_2$ONO$_2$ | ($R_{13}$); |
| —CH$_2$CH$_2$ONO$_2$ | ($R_{14}$); |
| —C(=NOH)(CH$_2$)$_3$ONO$_2$ | ($R_{15}$); |
| —CH$_2$CH(ONH$_2$)CH$_2$ONO$_2$ | ($R_{16}$); |

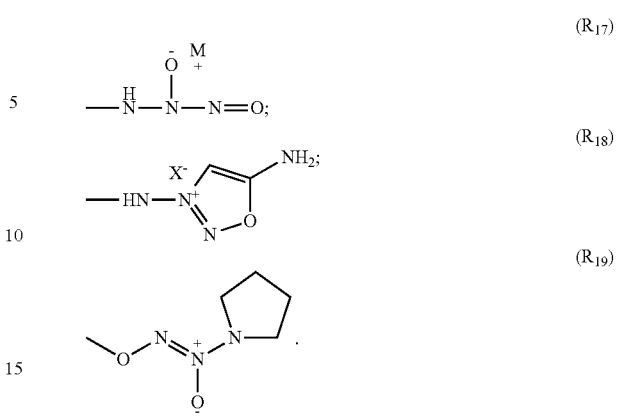

For Factor VIIa inhibitor II, the group $R_2$ is either hydrogen (H) (denoted as $R_{20}$) or any of the following NO donors:

| | |
|---|---|
| O=N—S | ($R_{21}$); |
| —ONO$_2$ | ($R_{22}$); |
| —CH$_2$ONO$_2$ | ($R_{23}$); |
| —CH$_2$CH$_2$ONO$_2$ | ($R_{24}$); |
| —C(=NOH)(CH$_2$)$_3$ONO$_2$ | ($R_{25}$); |
| —CH$_2$CH(ONH$_2$)CH$_2$ONO$_2$ | ($R_{26}$); |

Any of the preceding Factor VIIa inhibitors I, II, III, and IV may be comprised by a nanoparticle of the present invention such that the nanoparticle comprises a poly L-arginine polymer and the Factor VIIa inhibitor (I, II, III, and/or IV) in the poly L-arginine polymer.

Any of the preceding Factor VIIa inhibitors I, II, III, and IV may be comprised by a chemical structure of the present invention such that the chemical structure comprises the Factor VIIa inhibitor (I, II, III, and/or IV) that includes at least one nitric oxide (NO) donor.

For the preceding Factor VIIa inhibitors I, II, III, and IV, the linkage of the NO donor to the poly L-arginine polymer is between the amino or carboxyl groups and the hydroxyl or other reactive group.

Figure 1B:
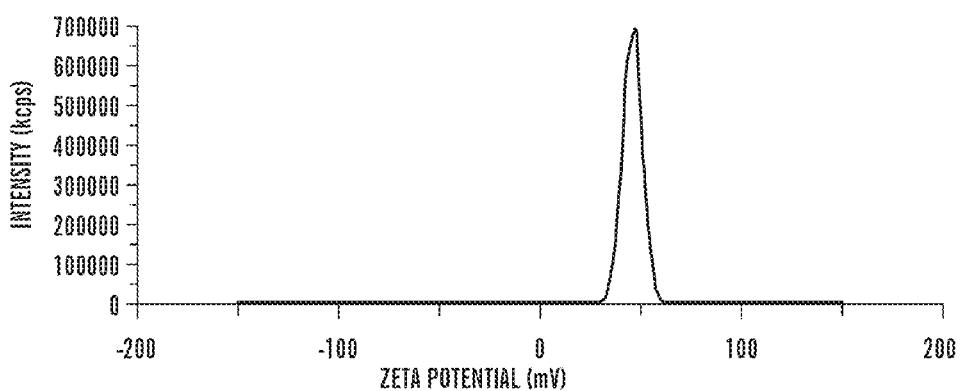

FIGS. 1A and 1B depict plots of the intensity of scattered nanoparticles versus (i) particle diameter size in nanometers (FIG. 1A) and (ii) Zeta potential due to surface charge (FIG.

1B), for Factor VIIa inhibitor (or Factor VIIa inhibitor-NO) encapsulated in poly L-arginine nanoparticles, in accordance with embodiments of the present invention. The plots of FIGS. 1A and 1B were derived from dynamic light scattering (DLS) measurements. The poly L-arginine nanoparticles encapsulating either Factor VIIa inhibitors or Factor VIIa inhibitors-NO donor may be optimized as to size and entrapment efficiency to get an optimum formulation with maximum loading based on the Factor VIIa inhibitor, Factor VIIa inhibitors-NO donor, or other active compounds to be utilized. The measured average diameter size is 380 nanometers and the average measured Zeta potential is 45.5 millivolts.

Figure 2A:
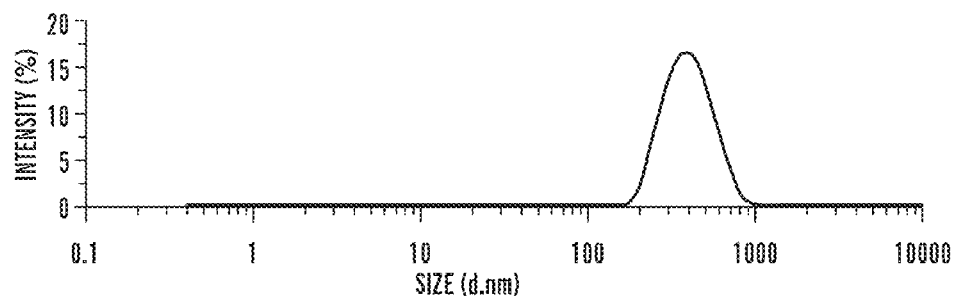
FIGS. 2A and 2B depict the intensity of scattered nanoparticles versus (i) particle diameter size in nanometers (FIG. 2A) and Zeta potential due to surface charge (FIG. 2B, for Factor VIIa inhibitor (or Factor VIIa inhibitor-NO) encapsulated in poly L-arginine (PLA)—fatty acid (lauric acid) nanoparticles, in accordance with embodiments of the present invention.
Figure 2B:
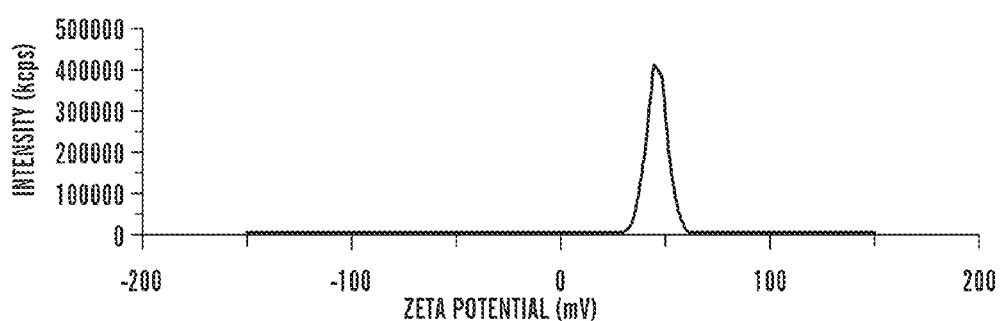

FIGS. 2A and 2B depict the intensity of scattered nanoparticles versus (i) particle diameter size in nanometers (FIG. 2A) and Zeta potential due to surface charge (FIG. 2B, for Factor VIIa inhibitor (or Factor VIIa inhibitor-NO) encapsulated in poly L-arginine—fatty acid (lauric acid) nanoparticles, in accordance with embodiments of the present invention. The plots of FIGS. 2A and 2B were derived from dynamic light scattering (DLS) measurements. The measured average diameter size is 345 nanometers and the average measured Zeta potential is 44.4 millivolts.

Figure 3A:
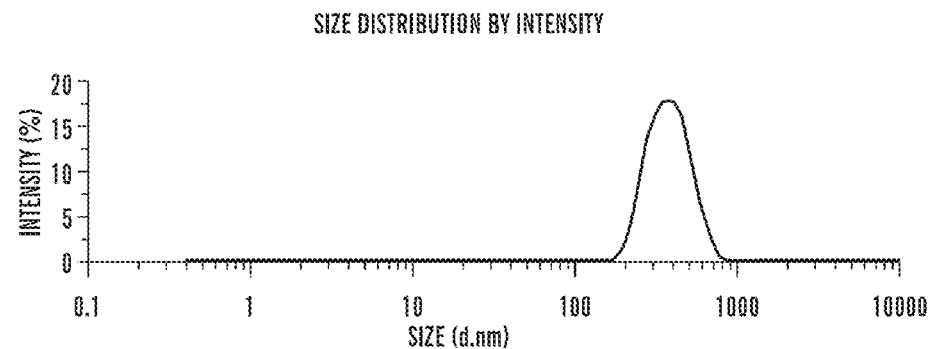
FIGS. 3A and 3B depict the intensity of scattered nanoparticles versus (i) particle diameter size in nanometers (FIG. 3A) and (ii) Zeta potential due to surface charge (FIG. 3B), for Factor VIIa inhibitor (or Factor VIIa inhibitor-NO) encapsulated in gluteraldehyde crosslink poly L-arginine nanoparticles, in accordance with embodiments of the present invention.
Figure 3B:
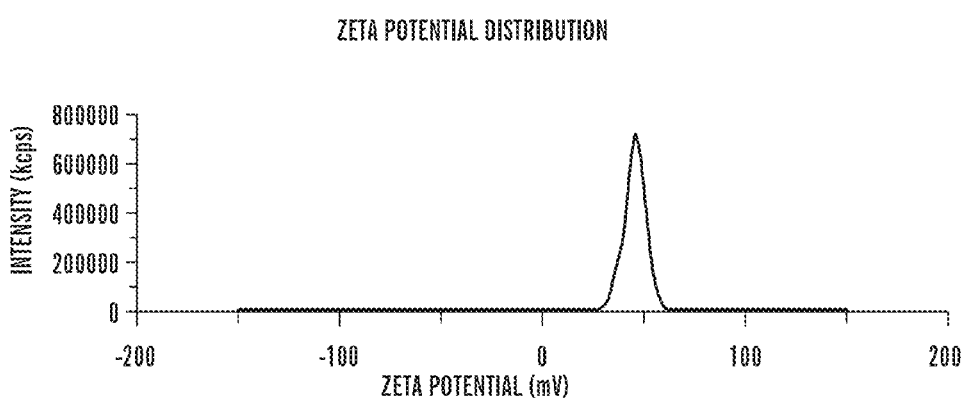

FIGS. 3A and 3B depict the intensity of scattered nanoparticles versus (i) particle diameter size in nanometers (FIG. 3A) and (ii) Zeta potential due to surface charge (FIG. 3B), for Factor VIIa inhibitor (or Factor VIIa inhibitor-NO) encapsulated in gluteraldehyde crosslink poly L-arginine nanoparticles, in accordance with embodiments of the present invention. The plots of FIGS. 3A and 3B were derived from dynamic light scattering (DLS) measurements. The measured average diameter size is 337 nanometers and the average measured Zeta potential is 45.8 millivolts.

Figure 4:
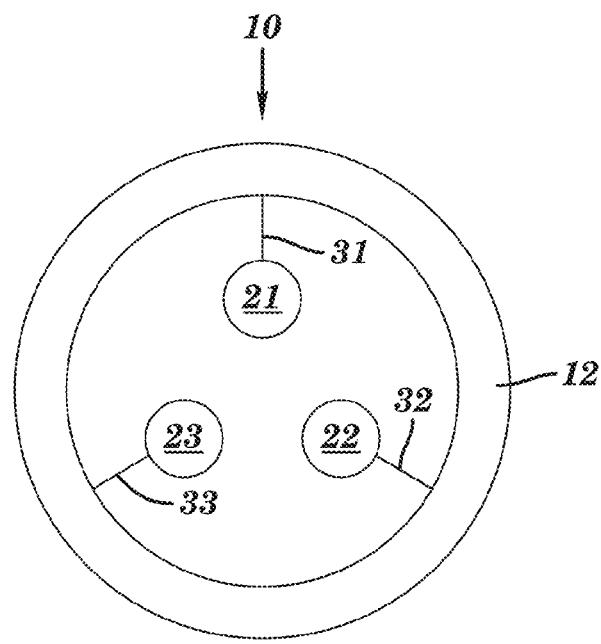
FIG. 4 depicts a nanoparticle, comprising a poly L-arginine polymer and Factor VIIa inhibitors conjugated to the poly L-arginine polymer and covalently bonded to the poly L-arginine polymer via covalent bonds, in accordance with embodiments of the present invention.

FIG. 4 depicts a nanoparticle 10, comprising a poly L-arginine polymer 12 and Factor VIIa inhibitors 21, 22, and 23 conjugated to the poly L-arginine polymer 12 and covalently bonded to the poly L-arginine polymer 12 via covalent bonds 31, 32, and 33, respectively, in accordance with embodiments of the present invention. The Factor VIIa inhibitors 21, 22, and 23 may be any of the Factor VIIa inhibitors identified supra, which includes Factor VIIa inhibitors with or without at least one NO donor. Although three Factor VIIa inhibitors (21, 22, 23) are depicted in FIG. 4, the nanoparticle 10 may generally comprise N1 Factor VIIa inhibitors such that N1 is a positive integer of at least 1.

Figure 5:
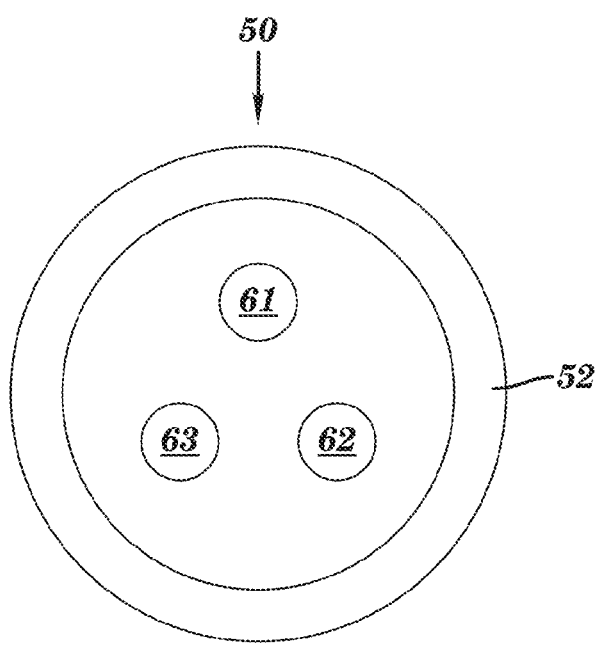
FIG. 5 depicts a nanoparticle, comprising a poly L-arginine polymer and Factor VIIa inhibitors encapsulated in the poly L-arginine polymer and not covalently bonded to the poly L-arginine polymer, in accordance with embodiments of the present invention.

FIG. 5 depicts a nanoparticle 50, comprising a poly L-arginine polymer 52 and Factor VIIa inhibitors 61, 62, and 63 encapsulated in the poly L-arginine polymer 52 and not covalently bonded to the poly L-arginine polymer 52, in accordance with embodiments of the present invention. The Factor VIIa inhibitors 61, 62, and 63 may be any of the Factor VIIa inhibitors identified supra, which includes Factor VIIa inhibitors with or without at least one NO donor. Although three Factor VIIa inhibitors (61, 62, 63) are depicted in FIG. 5, the nanoparticle 50 may generally comprise N2 Factor VIIa inhibitors such that N2 is a positive integer of at least 1.

Factor VIIa inhibitors or Factor VIIa inhibitors-NO donor encapsulated in nanoparticles with different degree of cross linking are tested for optimal pharmacokinetics. The formulation is optimized for loading efficiency. The ratios of different constituents are manipulated for optimum delayed release. To achieve that goal, the following parameters are evaluated: (i) particle size analysis by DLS spectroscopy; (ii) zeta potential measurement; (iii) in vitro release kinetics; (iv) Transmission Electron Microscopy for size confirmation, measurement of Factor VIIa inhibitors or Factor VIIa inhibitors-NO donor inside the nanoparticles (by HPLC or LC/MS).

Releasing NO from Poly L-arginine nanoparticles and its cross-linked materials having factor VIIa inhibitor encapsulated or Factor VIIa inhibitors conjugated with NO donors may be used for treating vascular disorders including pulmonary hypertension, pulmonary arterial hypertension, sickle cell disorders and other vascular disorders. Such nanoparticles provide improved delivery of Factor VIIA inhibitor-NO donor and allow for acute treatment and optionally for sustained release of Factor VIIA inhibitor-NO donor in a subject.

The long acting effective Factor VIIa inhibitors in nanoformulations that generate NO or Factor VIIa conjugated to NO donors, as provided in the present invention, expands the scope of aerosol (inhalation), oral and injectable therapies for treatment of pulmonary and other systemic vascular diseases such as sickle cell, peripheral artery diseases, critical limb ischemia, acute coronary syndrome, stroke, ischemia, and other vascular disorders.

SYNTHESIS EXAMPLES

Example 1

Synthesis of Factor VIIa Inhibitors or Factor VIIa Inhibitors-NO Donor Encapsulated Nanoparticles Nanoparticles encapsulating Factor VIIa inhibitors of the present invention are produced using a reverse micelle method where chitosan polymer and Factor VIIa inhibitors or Factor VIIa inhibitors. NO donors are added to Dimethysulfoxide (DMSO) and surfactant solution to form reverse micelles. Bifunctional reagent gluteraldehyde is added to this reverse micelles system as a cross-linking agent. The chemical cross-linking of poly L-arginine polymers with gluteraldehyde occurs by Schiff's reaction of aldehyde group on gluteraldehyde and amino group on the chitosan chain. Finally nanoparticles are separated out by high speed centrifugation.

Example 2

Synthesis of Poly L-arginine—PLGA Nanoparticles

Factor VIIa inhibitors or Factor VIIa inhibitors-NO donor PLA-PLGA hybrid nanoparticles are prepared according to the same scheme shown in Example 1.

Example 3

Synthesis of Hydrophobic Poly L-Arginine with Site Directed Delivery to Pulmonary Tissues Conjugation of ligand to the integrin αvβ3 such as cyclic N-Methyl-Arginine-Glycine-Aspartic acid (N-ME-Arg-Gly-Asp), and other known high affinity ligands to αv integrin Example 4

Synthesis of Hydrophobic Chitosan Polymer

Hydrophobic chitosan polymer is synthesized by cross-linking to fatty acids, amino acid, bile acid, poly glycol lactic acid, and other acids.

Example 5

Synthesis of Poly L-Arginine Cross Linked Nanoparticles

Nanoparticle formulations of Poly L-arginine with fatty acid, bile acid, bile salt, chitosan, PLGA or other amino acids were stirred, centrifuged, dialyzed, and Lyophilized. The lyophilized nanoformulations were measured for size and zeta potential by dispersing it in double distilled water or phosphate buffered saline. Nanoformulations were sonicated and stirred, checked repeatedly over time for size and Zeta potential.

Example 6

Synthesis of Chitosan (CS) Poly L-Arginine (PAR) Conjugate (CS-PAR)

The Chitosan poly L-arginine (CS-PAR) conjugates are synthesized where the conjugation is achieved by amide bond linkage between the amine group (—$NH_2$) of CS and the carboxyl group (—COOH) of PAR. Briefly, for conjugation of CS and PAR, 5 ml of CS solution (1 mg/ml) is mixed with 5 ml of PLR (1 mg/ml) and then added to 800 mg of 1-ethyl-3-(3-dimethylaminopropyl) carbodiimide hydrochloride (EDC) and 1 gram of N-hydroxysulfosuccinimide (Sulfo-NHS). After 24 hours, the resulting CS-PLR conjugates are separated by membrane-filter. Further dialysis will be performed for purification. The final solution is lyophilized for further studies.

Figure 6:
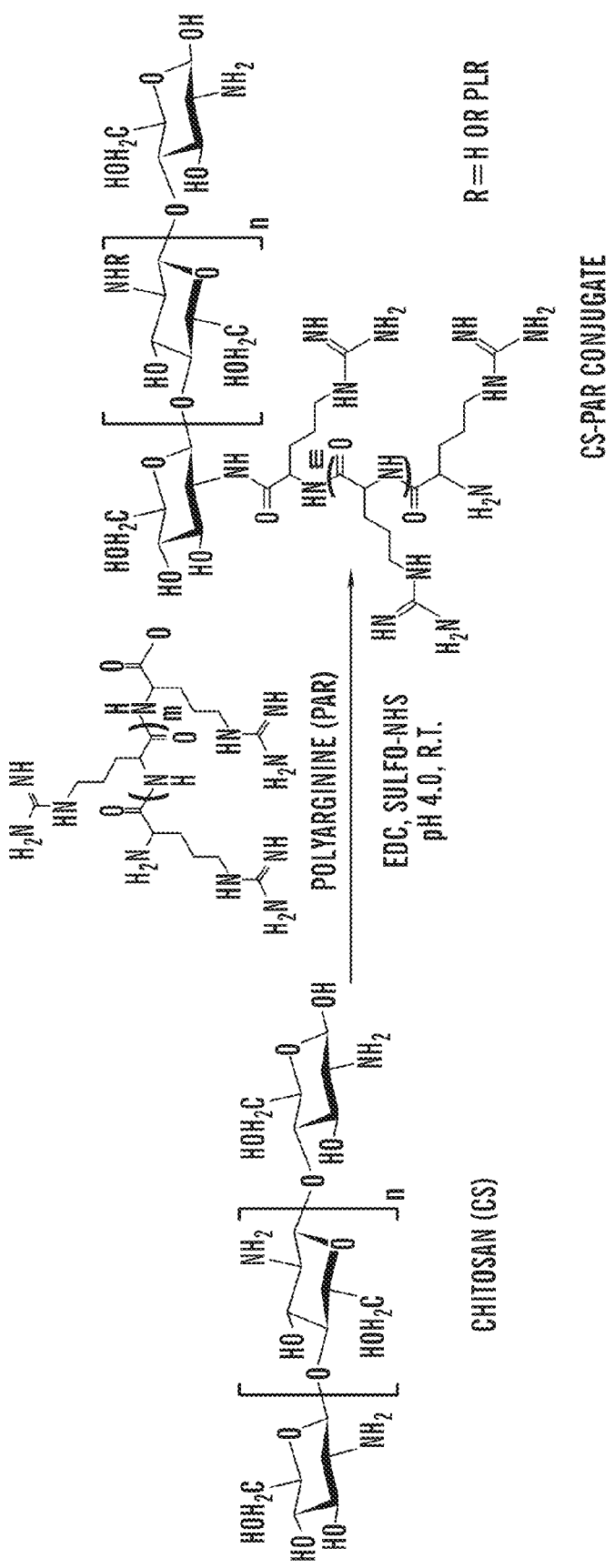
FIG. 6 depicts synthesis of chitosan-poly L-arginine conjugate, in accordance with embodiments of the present invention.

FIG. 6 depicts synthesis of chitosan-poly L-arginine conjugate, in accordance with embodiments of the present invention. The number of repeating unit (n) is in a range of 20-1000. The number of repeating units (m) is in a range of 10-500.

The same protocol is used for the conjugation of Poly L-arginine with PLGA (having $NH_2$ functional groups) via the COOH of the poly L-arginine. Additionally, conjugation of poly L-arginine with fatty acids or bile acids is through the $NH_2$ of the poly L-arginine.

Example 7

Synthesis of Chitosan-Poly L-Arginine Nanoparticles (CS-PAR-NPs)

A Chitosan-Poly L-arginine nanoparticle (CS-PAR-NPs) is synthesized in mild acidic conditions by promoting the interaction of the $NH_3$ group present in chitosan with the phosphate group present in tripolyphosphate (TPP). Briefly, to 10 ml of a solution 1% CS-PAR conjugate, 1 ml of a triphosphate disodium salt (1 mg/ml in DI water) is added drop by drop, with constant stirring. The entire solution is then sonicated for about 30 seconds using a probe sonicator, and allowed to stir for another 4 hours (approx). This solution is lyophilized to get the nanoformulation in powdered form. The lyophilized powder will be re-dispersed in phosphate buffered for further use.

Example 8

Synthesis of Factor VIIa Inhibitors with Poly-L-Arginine

Poly L-arginine (PAR) and Factor VIIa inhibitors are immersed in a 1% solution including (fatty acid, bile acid, amino acid, PLGA or chitosan), followed by stirring and sonicating; and performing a dialysis step, to yield the Factor VIIa inhibitors. The formed PAR layer formed in the Factor VIIa inhibitor may be cross linked with a cross linker (e.g., gluteraldehyde).

Treatment of Vascular Disorders

The following sections pertain to the treatment of vascular disorders (sickle cell disease, stimulated or pathological angiogenesis associated disorders, ocular angiogenesis-mediated disorders, coagulation and/or platelet activation disorders, pulmonary hypertension) and associated testing using Factor VIIa inhibitors I, II, II, and IV, also denoted as treatment compounds A, B, C, and D, respectively. In the tests described in the following sections on vascular disorders, it is to be understood that: (i) each compound (A, B, C, D) has the groups $R_1$ and $R_2$ at position 4 in the respective benzene ring; (ii) in each compound (A, B, C, D) with NO, the groups $R_1$ and $R_2$ are each the NO donor $R_{13}$ which is —$CH_2ONO_2$; (iii) each compound (A, B, C, D) in Poly L-arginine denotes each compound (A, B, C, D) encapsulated into, but not covalently bonded with, a Poly L-arginine nanoparticle such that the Poly L-arginine nanoparticle is cross-linked to chitosan in a L-arginine to chitosan ratio of 1/1; (iv) NO donor or without NO donor denotes that $R_1$ and $R_2$ are hydrogen in each compound (A, B, C, D); (v) as inferred from the test results, a therapeutic amount (i.e., dose) of compound (A, B, C, D) for treating any of the described vascular disorders is in a range of 0.1-10 mg per kilogram of body weight of the subject in each formulation (e.g., from factor VIIa inhibitors with NO donor and encapsulated in Poly L-arginine conjugated with L-arginine to chitosan 1/1 ratio), said dose achieving 1-10 uM for the various in vivo settings. A subject is defined to be a human being or a mammal. In one embodiment, the subject is a human patient.

The appearance of "1/1" in tables and elsewhere herein means L-arginine to chitosan ratio of 1/1.

The methods of treatment of the present invention include inhibiting vascular disorders in sickle disease subjects along with its thrombosis complication.

The methods of treatment of the present invention include inhibiting vascular disorders in scleroderma subjects along with its inflammatory and thrombosis complication.

The methods of treatment of the present invention include inhibiting accelerated or pathological angiogenesis such as the case in cancer, diabetic retinopathy, macular degeneration, inflammatory disorders, and other vascular abnormalities such as rosacea, psoriasis, and scleroderma.

The methods of treatment of the present invention include administrating therapeutic amount in the range of 0.1-10 mg/kg from factor VIIa inhibitors with NO donor and encapsulated in Poly L-arginine conjugated with L-arginine to chitosan 1/1 ratio. The administered dose will allow for achieving 1-10 ug/ml for the various in vivo settings.

The methods of treatment of the present invention include treating neointimal or plexiform lesion formation in lung vascular tissue, the methods comprising administering a therapeutic agent that inhibits tissue factor/factor VIIa activity (via the anti-factor VIIa) and its downstream signaling pathway along with vasodilation of constricted pulmonary vascular beds (via the NO donor and the poly L-arginine biodegradable nanoparticles.

The methods of treatment of the present invention can be used for treating pulmonary hypertension (PH) and pulmonary arterial hypertension (PAH) with or without other commonly used therapeutics.

In accordance with the present invention, the combination with other standard anti-PH or PAH include: Endothelin antagonist, phosphor diesterase inhibitors, calcium channel blockers, and other commonly used drugs.

The methods of treatment of the present invention include administering the composition via inhalation, intranasal, topically, orally, transdermally, parenterally, subcutaneously, intravenous injection, intra-arterial injection, and/or intramuscular injection.

Treatment of Sickle Cell Disease

Important factors that play a role in the clinical picture in the vascular disorder of sickle cell disease (SCD), endothelial adhesion, vascular tone, inflammation, pro-coagulation, and nitric oxide (NO) depletion. Given these abnormalities, the present invention utilizes an effective approach in fixing these alterations with factor VIIa inhibitors conjugated with Nitric Oxide (NO) donors and encapsulated/conjugated with a Poly L-Arginine with various cross linking with fatty acid, bile acid, chitosan, or combinations of thereof. With the novel compositions of the present invention, there are more options for interventional-targeted therapy to reduce the sickle disease morbidity and mortality.

Sickle red blood cells interact abnormally with the vascular endothelium, and this is thought to be one of the primary initiating factors in the development of micro-vascular occlusions in sickle cell disease. Sickle red blood cells (RBC) stay persistently bound to the endothelium despite an increase in shear force inside the vessels, which is opposite to the behavior of normal RBCs. Different pathways may explain the consequences of sickle RBCs' abnormal interaction including the sickle rigid cells being trapped inside the blood vessels, which leads to polymerization of HbS and obstructs the arteries and the sickle cells' adhesion, increases the activity of the nuclear factor KB and endothelin-1, and up-regulates vascular cell adhesion molecule (VCAM) and intercellular adhesion molecule (ICAM) adhesion molecules' activity, which result in vessel wall injury, remodeling, and occlusion. Furthermore, hemolysis in sickle cell subjects creates NO deficiency accelerating constriction of blood vessels, which further accelerate painful crisis along with its associate complications (Platt O S, Thorington B D, Brambilla D J, et al. Pain in sickle cell disease. Rates and risk factors. *N Engl J Med.* 1991; 325(1):11-6).

It is well known that hemolysis plays an integral part in sickle cell anemia. Its role is due to the accumulation of cell-free hemoglobin, leading to NO conversion to the inactive metabolites nitrate and methemoglobin, making it ineffective in controlling vessel tone. Recurrent episodes of vaso-occlusion and reperfusion play a major role in the pathogenesis of vascular injury in sickle cell anemia. All of this leads to vasoconstriction and platelet aggregation, and contributes to vascular dysfunction in sickle cell disease.

Activation of the coagulation system is significant in sickle cell disease pathogenesis. Studies showed that patients with sickle cell disease are more likely to have ischemic stroke and pulmonary embolism due to thrombosis development. Additionally, in sickle cell patients there is evidence of platelet activation and monocytes' abnormal expression of tissue factor (Beurling-harbury C, Schade S G. Platelet activation during pain crisis in sickle cell anemia patients. *Am J Hematol.* 1989; 31(4):237-41; Shet A S, Aras O, Gupta K, et al. Sickle blood contains tissue factor-positive microparticles derived from endothelial cells and monocytes. *Blood.* 2003; 102(7): 2678-83). Exposure of phosphatidylserine of sickle cell's membrane is another factor that might contribute to the hyper-coaguable state by activation of prothrombin (Setty B N, Rao A K, Stuart M J. Thrombophilia in sickle cell disease: the red cell connection. *Blood.* 2001; 98(12):3228-33).

Example 9

Human Endothelial Cells (ECs)

Using gelatin-coated culture flasks, Human Umbilical Vein Endothelial Cells (HUVEC) were cultured in Endothelial Cell Growth Medium (EGM) complete media supplemented with 2 ml bovine brain extract, and passaged when 80% confluent using trypsin/EDTA solution according to the manufacturers' instructions. Cells from passages 2 to 6 were used for adhesion assay experiments. Cells were sub-cultured in a 96-well plate pre-coated with collagen with a number of 20,000 cells per well, and were left for 24 hours at 37° C. in a $CO_2$ (5%) incubator to form a confluent monolayer.

Example 10

Preparation of Packed RBCs Separation

Normal and sickle blood samples were collected in EDTA tubes from healthy volunteers and homozygous sickle cell patients, respectively. RBCs were separated from whole blood by centrifugation (1000×g for 10 minutes), and plasma was collected and stored at −80° C. Packed RBCs were washed once with Phosphate Buffered Saline (PBS), and counted using a CBC analyzer. Then $50 \times 10^6$ single red blood cells were transferred into a 15 ml conical tube, and re-suspend into 5 ml PBS. Finally the cells were centrifuged at 1000×g for 10 minutes to yield a loose pellet.

Example 11

RBC Labeling

Normal and sickle RBCs were labeled using the PKH67 green fluorescent cell linker kit according to the manufacturer's instructions. Briefly, 50 μl ($50 \times 10^6$ cells) of single red blood cells were incubated with 4 μl PKH67 dye in 2 ml diluent C for 5 min at room temperature with periodic mixing. The staining was stopped by adding 2 ml of 1% BSA for 1 minute and the cells centrifuged at 1000×g for 10 minutes. The supernatant was removed, and the packed RBC pellet was washed 4 times by centrifugation in complete medium to ensure removal of unbound dye. After the final wash, the packed RBC pellet was resuspended in complete medium to yield a final concentration of $1 \times 10^7$ cells/ml.

Example 12

Static Cell-Cell Adhesion Assay

After HUVECs formed a confluent monolayer in the plate's wells, the experiment was designed to include five groups in triplicate: medium only (negative control), TNF-α only (positive control), or TNF-α with the treatment compounds: LMWH, NACH, and PSI. All ECs except the negative control group were treated with TNF-α (10 ng/ml) for 1 hour to increase the expression of adhesion molecules like ICAM, VCAM, P- and E-selectin on the ECs' surface. HUVECs were rinsed with PBS and 200 μA of media were added to each well. Both HUVECs and labeled RBCs were incubated with treatment compounds (compounds A-D, compounds A-D encapsulated into Poly L-arginine, compounds A-D having NO donors, or compounds A-D having NO donor and encapsulated into Poly L-arginine) for 45 min at 37° C. The media were removed from the plate's wells and 200 μA of labeled RBCs ($2 \times 10^6$ cells) were added to each well and incubated at 37° C. for 45 minutes. Non-adherent RBCs were removed with PBS wash, and then 150 μl of complete medium were added for plate reading. Plates were read in fluorescence mode on a BioTek® micro-plate reader at excitation 485 nm and emission 528 nm and analyzed by the in-built software. The number of bound PKH67-labeled RBCs in each sample was calculated from the corresponding standard RBC curve using Excel software.

Example 13

Static Adhesion Assay

Initial efforts were directed to optimize the protocol of RBCs adhesion assay. HUVECs monolayer was at least >90% confluent to prevent the adhesion of RBCs to the base of the wells. Blood was collected in EDTA tubes and packed RBCs were used without contamination by platelets or leukocytes as measured by the CBC analyzer. PKH67 labeling of RBCs was uniform, intense, with no leaking or cytotoxicity observed (see FIGS. 7A and 7B).

Figure 7A:
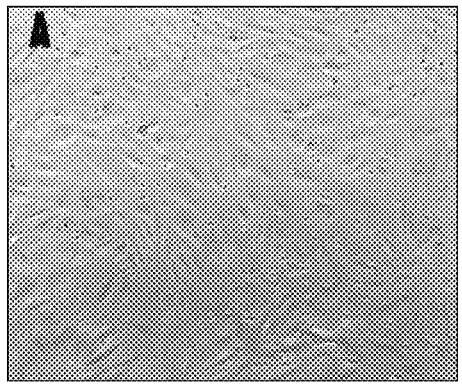
FIGS. 7A and 7B depict Human Umbilical Vein Endothelial Cells (HUVEC) monolayer and labeling of red blood cells, in accordance with embodiments of the present invention.
Figure 7B:
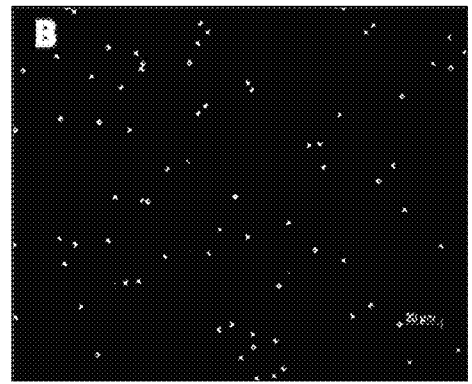

FIGS. 7A and 7B depict HUVECs monolayer and labeling of RBCs, in accordance with embodiments of the present invention. In FIG. 7A, HUVECs monolayer is greater than 90% confluent to prevent RBCs from adhering to the base of the wells. Small rounded cells on top of HUVECs are bound RBCs. In FIG. 7B, bound RBCs are labeled with PKH67 green dye. In contrast with FIG. 7A, all RBCs in FIG. B show intense labeling with no leaking of the dye to HUVECs cells.

Comparing the binding of normal and sickle RBCs to endothelial layer under static conditions, normal cells did not show any significant adherence to endothelial cells. In contrast, sickle RBCs demonstrated significantly higher adhesion by almost 10-fold. By treating endothelial cells with 10 ng/ml of TNF-α to induce the expression of adhesion molecules, both types of RBCs showed significant increase in adhesion with higher values in sickle RBCs (see FIG. 8).

Figure 8:
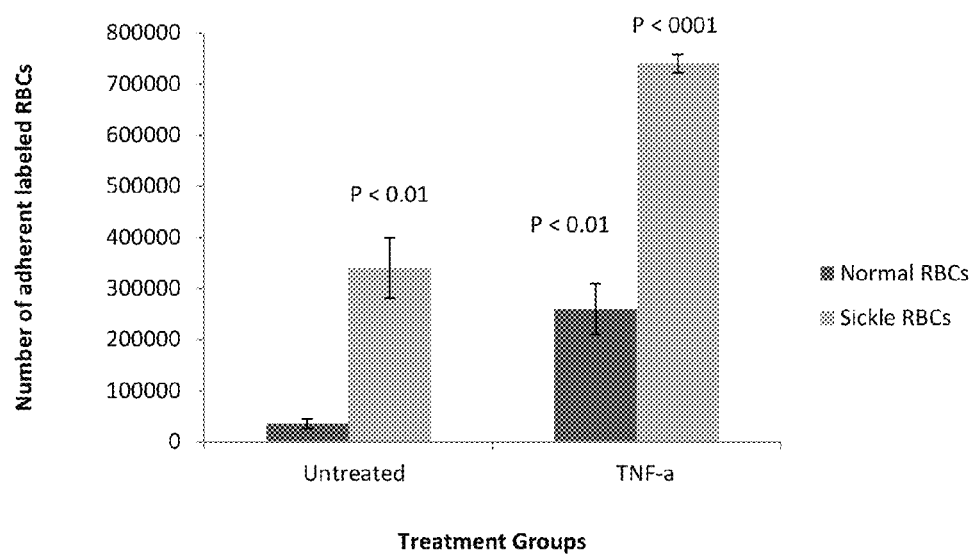
FIG. 8 depicts adherence of normal and sickle red blood cells adhesion to endothelial cells with or without TNF-α treatment, in accordance with embodiments of the present invention.

FIG. 8 is a graph depicting adherence of normal and sickle RBCs adhesion to endothelial cells with or without TNF-α treatment, in accordance with embodiments of the present invention. Normal cells did not show any significant adherence to endothelial cells. In contrast, sickle RBCs demonstrated significantly higher adhesion by almost 10-fold. By treating endothelial cells with 10 ng/ml of TNF-α to induce the expression of adhesion molecules, both types of RBCs showed significant increase in adhesion with higher values in sickle RBCs. The error bars show the standard deviations of the mean adherence values.

Table 3 infra depicts data represent average % inhibition of RBC adhesion to endothelial cells. Compounds A-D (with NO) at 1-10 µM did not have any significant effect on RBC/EC adhesion. In contrast, compounds A-D (with NO) encapsulated into Poly L-Arginine nanoparticles resulted in 20-30% inhibition of RBC/EC adhesion at 1 µM. All compounds listed were tested at 1.0 µM. Listed compounds demonstrated 100% inhibition at 3 µM.

TABLE 3

Effect of Inhibitors of Factor VIIa - NO Nanoformulation on Sickle RBC-EC Adhesion

| Compounds | Mean % Inhibition of Sickle RBC-EC Adhesion ± SEM |
| --- | --- |
| A-NO | 65 ± 6 |
| B-NO | 72 ± 5 |
| C-NO | 75 ± 7 |
| D-NO | 81 ± 6 |
| A-NO NP | 95 ± 4 |
| B-NO NP | 100 ± 0 |
| C-NO NP | 97 ± 3 |
| D-NO NP | 100 ± 0 |

The compounds listed in Table 3 were tested at 1.0 µM

The data in Table 3 represent average % inhibition of RBC adhesion to endothelial cells. Compounds A-D at 1.0 µM did not have any significant effect on RBC/EC adhesion. In contrast, A-D NP (encapsulated into Poly L-Arginine) resulted in 20-30% inhibition of RBC/EC adhesion at 1 µM. All compounds listed were tested at 1.0 µM. Listed compounds demonstrated 100% inhibition at 3 µM.

Summary of Anti-Angiogenesis Efficacy and Anti-Coagulant Effects

Studies conducted in conjunction with the present invention demonstrated the anti-angiogenesis efficacy that would have an impact in tumor progression and cancer metastasis (oncological applications) and ocular-mediated disorders such as diabetic retinopathy and age-related macular degeneration. The anti-coagulant effects of Factor VIIa small molecule inhibitors would have an impact on venous thrombosis including deep vein thrombosis (DVT), pulmonary embolism (PE), and cancer-associated thrombosis. Additionally, the antiplatelet effects were demonstrated with NO donor conjugated factor VIIa inhibitors and enhanced further when encapsulated into Poly L-Arginine-chitosan nanoformulations with L-arginine to chitosan 1/1 ratio, which would have an impact on arterial thrombosis. These data indicate a potential utility in both arterial and venous thromboembolic disorders including DVT, PE as well as acute coronary syndromes such as heart attack, stroke and peripheral artery diseases. The factor VIIa inhibitor with or without NO donor encapsulated into Poly L-Arginine-chitosan (with L-arginine to chitosan 1/1 ratio) are expected to yield 1-10 ug/ml blood levels when administered at doses ranging from 0.1-10 mg/Kg.

Furthermore, the antithrombotic efficacy along with the NO and Poly L-Arginine vasodilator efficacy would play a major role in benefiting pulmonary hypertension subject populations, acute myocardial infarction, stroke, peripheral artery diseases, and subjects with cardiac insufficiency.

Treatment of Stimulated or Pathological Angiogenesis Associated Disorders

Efficacy of factor VIIa inhibitors in inhibiting angiogenesis-mediated by various pro-angiogenesis factors:

Example 14

Chick Chorioallantoic Membrane (CAM) Model of Growth Factor & TF/VIIa-Induced Angiogenesis Neovascularization is examined. Ten-day old embryos purchased from Spafas, Inc. (Preston, Conn.) and incubated at 37° with 55% relative humidity were used in this investigation. A small hole is punctured in the shell concealing the air sac with a hypodermic needle and a second hole was punctured in the shell on the broadside of the egg directly over an avascular portion of the embryonic membrane, as observed during candling. A false air sac was created beneath the second hole by the application of negative pressure to the first hole, which causes the chorioallantoic membrane (CAM) to separate from the shell. A window, approximately 1.0 cm², were cut in the shell over the dropped CAM with the use of a small crafts grinding wheel (Dermal, Division of Emerson Electric Company Racine, Wis.) allowing for direct access to the underlying CAM. Filter disks of #1 filter paper (Whatman International, United Kingdom) were soaked in 3 mg/ml cortisone acetate (Sigma, St. Louis, Mo.) in a solution of 95% ethanol and subsequently air dried under sterile conditions.

Fibroblast growth factor (FGF2), TF/VIIa or other growth factors such as vascular endothelial growth factor (VEGF) were used to grow vessels on the CAMs of 10-day old chick embryos. Sterile filter disks adsorbed with FGF2, VEGF, TF/VIIa dissolved in PBS are placed on growing CAMs. At 24 hours, test agent or control vehicle was added directly to CAMs topically.

The results are shown in Tables 4a, 4b, 4c, 5, 6, and 7.

TABLE 4a

Effect of Factor VIIa inhibitors on TF/VIIa-stimulated Angiogenesis in the CAM Model

| CAM Treatment | Branch points ± SEM | % Inhibition ± SEM |
|---|---|---|
| PBS (Control) | 99 ± 6 | |
| TF/VIIa (1/1 ug) | 215 ± 21 | |
| Compound A (1 ug) + TF/VIIa (1/1 ug) | 126 ± 10 | 74 ± 13 |

The data in Table 4a represent Mean±SEM, n=8 per group; 100% inhibition was achieved at 3-10 ug/CAM.

TABLE 4b

Effect of Factor VIIa inhibitors on FGF2-stimulated Angiogenesis in the CAM Model

| CAM Treatment | Branch points ± SEM | % Inhibition ± SEM |
|---|---|---|
| PBS (Control) | 99 ± 6 | |
| FGF2 (1 ug) | 180 ± 11 | |
| Compound A (1 ug) + FGF2 (1 ug) | 123 ± 10 | 70 ± 13 |

The data in Table 4b represent Mean±SEM, n=8 per group; 100% inhibition was achieved at 3-10 ug/CAM.

TABLE 4c

Effect of Factor VIIa inhibitors on VEGF-stimulated Angiogenesis in the CAM Model

| CAM Treatment | Branch points ± SEM | % Inhibition ± SEM |
|---|---|---|
| PBS (Control) | 99 ± 6 | |
| VEGF (1 ug) | 175 ± 11 | |
| Compound A (1 ug) + VEGF (1 ug) | 127 ± 10 | 74 ± 12 |

The data in Table 4c represent Mean±SEM, n=8 per group; 100% inhibition was achieved at 3-10 ug/CAM.

TABLE 5

Effect of Factor TF/VIIa inhibitors on TF/VIIa-stimulated Angiogenesis in the CAM Model

| CAM Treatment | Branch points ± SEM | Mean % Inhibition ± SEM |
|---|---|---|
| PBS (Control) | 96.1 ± 11.1 | |
| TF/VIIa (1/1 ug)) | 181.8 ± 10.7 | |
| Compound B (1 ug) + TF/VIIa (1/1 ug) | 110.4 ± 8.3 | 79.9 ± 11.8 |
| Compound C (1 ug) + TF/VIIa (1/1 ug) | 105.2 ± 9.7 | 82.8 ± 13.7 |
| Compound D (1 ug) + TF/VIIa (1/1 ug) | 112.3 ± 9.1 | 77.3 ± 12.9 |

The data in Table 5 represent Mean±SEM, n=8 per group; 100% inhibition was achieved at 3-10 ug/CAM.

TABLE 6

Effect of Factor VIIa inhibitors with or without NO donor/Poly L-Arginine NP (1/1 L-Arginine/Chitosan) on FGF2-mediated angiogenesis in the CAM model

| CAM Treatment | Branch points ± SEM | % Inhibition ± SEM |
|---|---|---|
| PBS (Control) | 49 ± 6.6 | |
| FGF2 (1 ug) | 122 ± 11.5 | |
| Compound B (1 ug) + FGF2 (1 ug) | 59 ± 6.6 | 83.9 ± 9.9 |
| Compound C (1 ug) + FGF2 (1 ug) | 57 ± 5.5 | 88.3 ± 8.1 |
| Compound D (1 ug) + FGF2 (1 ug) | 67 ± 4.6 | 72.3 ± 7.1 |
| Compound B-NO (1 ug) + FGF2 (1 ug) | 53 ± 6.4 | 95.2 ± 7.1 |
| Compound C-NO (1 ug) + FGF2 (1 ug) | 51 ± 5.6 | 98.9 ± 6.6 |

The data in Table 6 represent Mean±SEM, n=8 per group; 100% inhibition was achieved at 3-10 ug/CAM.

TABLE 7

Effect of Factor VIIa inhibitors - NO Donor on FGF2-Mediated Angiogenesis in The CAM Model

| CAM Treatment | Branch points ± SEM | % Inhibition ± SEM |
|---|---|---|
| PBS | 61.6 ± 6 | — |
| FGF2 (1 ug) | 157.8 ± 15 | — |
| Poly L-Arginine NP + FGF2 (1 ug) | 153 ± 10 | 05 ± 3 |
| Compound A (1 ug) + FGF2 (1 ug) | 101 ± 9 | 78.3 ± 8 |
| Compound A (1 ug) in Poly L-Arginine + FGF2 (1 ug) | 91.5 ± 6 | 85.6 ± 5 |
| Compound A - NO (1 ug) in Poly L-Arginine + FGF2 (1 ug) | 79.3 ± 5.7 | 94.5 ± 5 |

The data in Table 7 represent Mean±SEM, n=8 per group; 100% inhibition was achieved at 3-10 ug/CAM.

Tables 4a, 4b, and 4c show that compound A at 1 ug/CAM, in the presence of TF/VIIa, FGF2, and VEGF-stimulated angiogenesis, inhibits the angiogenesis by 70-74%.

Tables 5-7 show that compounds A-D exhibit 72-88% inhibition of angiogenesis, and that compounds A-C exhibit 94-99% inhibition of angiogenesis with NO or with NO in Poly L-arginine encapsulation.

Figure 9:
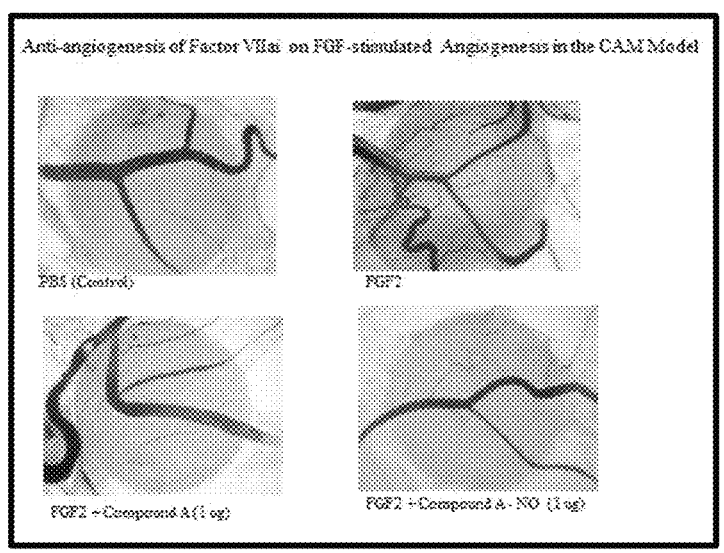
FIG. 9 depicts neovascularization images for the effect of inhibitor of Factor VIIa with or without NO donor in the Chick Chorioallantoic Membrane (CAM) model, in accordance with embodiments of the present invention.

FIG. 9 depicts neovascularization images for the effect of inhibitor of Factor VIIa with or without NO donor in the CAM Model, in accordance with embodiments of the present invention.

Example 15

CAM Tumor Growth and Angiogenesis Studies

For the tumor angiogenesis and tumor growth studies, pancreatic cancer cells were implanted topically into the CAM. Test compounds were added to cancer cell implant in matrigel at 10 ug/CAM to assess their ability to target the tumor or tumor vasculature. Tumors was excised and examined under a stereomicroscope at 50-× magnification. Digital images of was collected using a 3-CCD color video camera system and analyzed with Image-Pro Plus software. The numbers of vessel branch points were counted for each section. Portions of the tumor were extracted for hemoglobin determinations. Individual CAMs were harvested at various time points after administration of test compounds.

Table 8 depicts the effect of Inhibitors of factor VIIa with or without NO donor and/or encapsulated into Poly L-Arginine NP on pancreatic tumor growth in the CAM Implant Model. Data showed significant inhibition of tumor growth after 7 days of implant (Table 8). The data in the Tumor Weight column represents Mean±SEM, n=8 per group. SEM stands for Standard Error of the Mean.

TABLE 8

Effect of Factor VIIa inhibitors on Tumor growth

| CAM Conditions | Tumor Weight ± SEM (mg) |
|---|---|
| Panc-1 (1.0 × 10$^6$ cells/CAM) in Matrigel | 95 ± 8.1 |
| Panc-1 + A (10 ug/CAM) | 13 ± 3.1 |
| Panc-1 + A - NP (10 ug/CAM) | 11 ± 4.4 |
| Panc-1 + A-NO (10 ug/CAM) | 08 ± 1.1 |
| Panc-1 + A - NO NP (10 ug/CAM) | 05 ± 1.3 |

The data in Table 8 represent Mean±SEM, n=8 per group.

Example 16

Ocular Angiogenesis-Mediated Disorders

In a diabetic retinopathy study using an Oxygen Induced Retinopathy Model (ROP), litters of C57 black mice were obtained on post-natal day 5 (P5) and acclimated prior to placement in oxygen chambers on P7. Litters and dams were placed in oxygen chambers (75% O$_2$) in the morning of P7 with sufficient food and water for 5 days because chambers will not be opened for 5 days. Litters were distributed so that each dam had 8 pups because the number of nursing pups affects the development of neovascularization. Litters and dams were removed from oxygen chamber at day 12 (P12), and all the animals were weighed. The weight of the pups was monitored throughout the study and foster dams were substituted for original dams for any pups which weight 20% less than the other pups. Pups were euthanized on day 17 following isoflurane administration by severing their spinal cord in the neck region. Eyeballs were removed and kept on ice until fixation. For dissection of the eye, the eye was cut anterior to the limbus to preserve the ciliary body. Four cuts were made and the resulting leaves straightened. The preparation was fixed in 3.5% formaldehyde for 10 minutes, and then the sclera was removed with forceps, with the ciliary bodies left intact. The preparation was fixed for another 30 minutes, then placed in Phosphate buffered saline until staining was performed. In the staining procedure, preparations were incubated overnight in 0.5% Triton then rinsed 3 times in PBS. Preparations were placed in GS-lectin-Alexa solution (7 ug/ml) in 24-well plates and incubated in the cold for 1 hr. with shaking. After rinsing, preparations were mounted on slides for evaluation by immunofluorescence microscopy and digital image analysis to quantify the vessel area (mm2) on each retina.

Using the ROP Model, the effect of intravitreally injected (i-v) FVIIai on total area of retinal vascularization in mouse retinas was studied. The ROP model was used to study the effect of factor VIIai on the process of neovascularization. C57BL6 mouse were injected i-v under general isoflurane anesthesia with factor VIIai (0.01 mg) into both eyes. PBS was used as a control. Retinal area of vascularization (mm$^2$) was determined as described.

TABLE 9

Effect of Inhibitors of Factor VIIa with or without NO donor on retinal Neovascularization

| Compounds | Mean % Inhibition of retinal Neovascularization ± SEM |
|---|---|
| A | 51 ± 6 |
| A-NO | 62 ± 4 |

In Table 9, the data represent mean % inhibition of retinal neovascularization as compared to control. Compounds were tested at 0.01 mg intra-vitreal (i-v). Table 9 shows that compounds A with or without NO exhibited a 51-62% mean % inhibition of retinal neovascularization.

Example 17

Age-Related Macular Degeneration

For Choroidal Neovascularization (CNV) induction in rats, brown Norway rats were anesthetized and pupils dilated. Argon red laser photocoagulation (50-um spot size, 0.05 sec duration) was used to generate 4 laser spots for each eye surrounding the optic nerve. A bubble forms at the laser spot indicating rupture of Bruch's membrane. The laser spots were evaluated for the presence of CNV on day 10 after laser treatment using confocal microscopy. Administration of test compounds: Immediately after CNV induction, test compounds were given once by intravitreal injection, i-v (VIIa-i versus r-TFPI).

For characterization of efficacy in preventing laser-induced CNV in the eyes of rats, the incidence of CNV-positive or CNV-negative spots was determined by confocal microscopy. Rats were perfused with a FITC-dextran solution just prior to sacrifice. After the eyes were excised and choroidal flat mounts prepared, the mounts were stained with a mAb against mouse or rat elastin and then with CY3-conjugated secondary antibody. The prominent neovascular growth stains green whereas the underlying elastin in the Bruch's membrane stains red within the laser spot. The inhibition of new vessel growth is indicated by the absence of vessels with a green stain, and the size of the CNV is measured using Image Pro plus Software.

Figure 10:
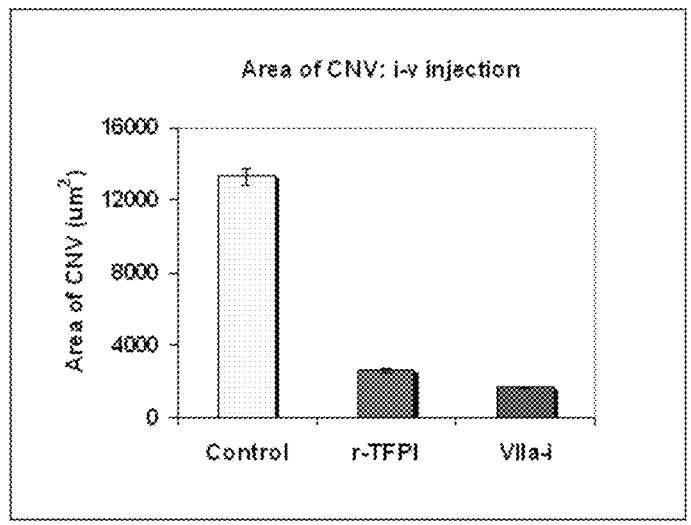
FIG. 10 is a graph depicting the effect of an inventive Factor VIIa inhibitor or r-TFPI administered on Laser-induced Choroidal Neovascularization (CNV), in accordance with embodiments of the present invention.

FIG. 10 is a graph depicting the effect of VIIa-i (Compound A-NO NP) or r-TFPI (recombinant tissue factor pathway inhibitor) administered i-v in Laser-induced CNV model, in accordance with embodiments of the present invention. CNV was induced as described in methods above. All i-v treatments were administered immediately after laser-induction on D0. Treatments were as follows: Control: PBS; r-TFPI: 0.2 ug; VIIa-i (Compound A-NO NP): 5.08 ug. Animals were sacrificed on D10, and CNV evaluated as described in methods. A single i-v injection of either treatment was highly effective in inhibiting laser-induced CNV, p<0.00001. FIG. 10 shows that Compound A with NO encapsulated within a Poly L-arginine nanoparticle significantly inhibits the CNV.

Figure 11:
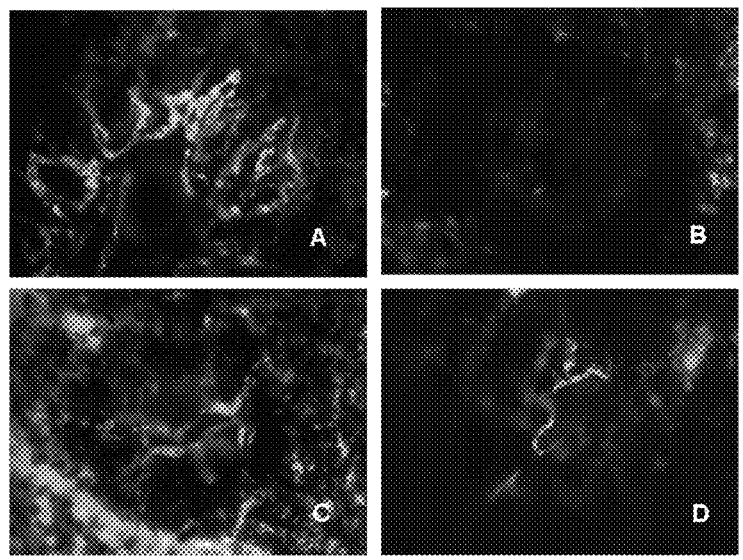
FIG. 11 depicts confocal images of CNV-Positive or CNV-negative spots in animals receiving Phosphate Buffered Saline (PBS) control or r-TFPI (recombinant Tissue Factor Pathway Inhibitor), in accordance with embodiments of the present invention.

FIG. 11 depicts confocal images of CNV-Positive or CNV-negative spots in animals receiving PBS (Control) or r-TFPI (recombinant Tissue Factor Pathway Inhibitor), in accordance with embodiments of the present invention. Rats were perfused with a FITC-dextran solution just prior to sacrifice. The prominent neovascular growth stained green. Inhibition of new vessel growth is indicated by the absence of vessels with a green stain. Image Pro Plus Software was used to quantify neovascular growth area as shown in FIG. 10 above. Two representative images for each treatment are shown. Panels A and C: i-v PBS Controls; B and D: i-v r-TFPI and Factor VIIai (Compound A-NO NP). Panels B and D show a significant reduction in neovascular growth as compared with the controls depicted in panels A and C.

Coagulation and/or Platelet Activation Disorders

The Factor VIIa inhibitors of the present invention may be used to treat both arterial and venous thromboembolic disorders including DVT, PE as well as acute coronary syndromes such as heart attack, stroke and peripheral artery diseases.

The anti-thrombotic effects of Factor VIIa inhibitors were determined using human blood using thrombelastography (TEG) or Platelet aggregation in human platelet rich plasma (PRP). The activated partial thromboplastin time (aPTT) and the prothrombin time (PT) assays are universally recognized clinical assays of the coagulation system. Thrombelastography was used to measure the efficacy of anti-VIIa in inhibiting platelet/fibrin clot dynamics.

Example 18

Activated Partial Thromboplastin Time (aPTT)

To 0.1 ml of citrated plasma 0.1 ml of human placenta lipid is added and the mixture is incubated for 2 min at 37° C. The coagulation process is initiated by the addition of 0.1 ml 25 mM calcium chloride and the time to clot formation is determined. The APTT measures effects on the endogenous pathway of coagulation.

All compounds A-D with or without NO donor or encapsulated into Poly L-Arginine nanoparticle (NP) resulted in a concentration-dependent significant prolongation of aPTT from baseline of 32+5 seconds to 100-200 seconds at 1-10 μM.

Example 19

Platelet Aggregation—Light Transmittance Aggregometry

For in vitro-assay, 40 ul of the test solution are added to samples of 320 ul PRP isolated from human subject's blood. The samples were inserted into the aggregometer and incubated at 37° C. for 2 min under continuous magnetic stirring at 1000×rpm. After the addition of 40 ul aggregating agent (Adenosine diphosphate at 20 uM), a change in optical density is monitored continuously until constant values for aggregation was achieved. The transmission maximum serves as a scale for platelet aggregation (0%=transmission of PRP, 100%=transmission of PPP). For in vitro-assays, percent inhibition of platelet aggregation is determined relative to vehicle controls. $IC_{50}$ values are determined from the non-linear curve fitting of concentration-effect relationships. $IC_{50}$ is defined as the concentration of test drug for half maximal inhibition of aggregation.

Only factor VIIa inhibitors A-D with NO donor or encapsulated into Poly L-Arginine NP resulted in a concentration-dependent significant inhibition of platelet aggregation mediated by Adenosine diphosphate (ADP), with an IC50 of 1-10 μM. In contrast, inhibitors of factor VIIa without NO or not encapsulated into Poly L-arginine did not have significant inhibitory effect on ADP-mediated platelet aggregation.

Example 20

Platelet-Fibrin Clot Kinetics

Thrombelastography (TEG) was performed in either citrated whole blood after re-calcification. The blood samples were mixed with 3.8% tri-sodium citrate solution (one part citrate solution to 9 parts blood) as anticoagulant. The citrated whole blood was re-calcified by adding 0.4 ml isotonic calcium chloride solution. An aliquot of 0.36 ml of the re-calcified whole blood was transferred to the pre-warmed cup of the thrombelastograph. The following measurements were the standard variables of TEG: (i) Reaction time (R): the time from sample placement in the cup until onset of clotting (defined as amplitude of 1 mm). This represents the rate of initial fibrin formation; (ii) Maximum amplitude (MA): greatest amplitude on the TEG trace, wherein MA represents the absolute strength of the fibrin clot and is a direct function of the maximum dynamic strength of fibrin and platelets.

Compounds A-D inhibited platelet-fibrin clot dynamics (see Table 10). Greater inhibition were shown with A-D having NO donors and/or encapsulated into Poly L-Arginine—Chitosan (1/1).

TABLE 10

Effect of Factor VIIa inhibitors on platelet-fibrin clot dynamics in human blood

| TEG Parameters | Control | A | B | C | D |
|---|---|---|---|---|---|
| | | | Mean ± SEM | | |
| R (minutes) | 9.7 ± 2.3 | 23.4 ± 1.4 | 25.6 ± 2.9 | 33.4 ± 1.2 | 44.4 ± 1.6 |
| MA (mm) | 58.2 ± 1.7 | 5.0 ± 2.0 | 6.5 ± 0.8 | 5.1 ± 2.4 | 3.4 ± 0.6 |

Table 10 pertains to citrated human whole blood plus 2.5 mM calcium. The data represent mean for n=3±SEM. Compounds A-C were tested at 1 ug/ml. Similar inhibitory effects on platelet-fibrin clot kinetics were shown for A-D with NO and with Poly L-arginine NP. 100% inhibition was achieved at 3 ug/ml.

Pulmonary Hypertension

Example 21

Rat Monocrotaline Model of Pulmonary Hypertension

This example is for a rat monocrotaline model of pulmonary hypertension. The rat monocrotaline model is a standard and well accepted model of pulmonary arterial hypertension (PAH). Improvement in pulmonary arterial hypertension from drug treatment in the rat monocrotaline model is predictive of therapeutic response in humans with PAH. Pulmonary arterial hypertension was induced in male Sprague Dawley rats with monocrotaline as carried out by Itoh et al (2004). Continuous monitoring of PA pressures was performed with telemetry system. In this model, severe pulmonary hypertension develops 3 weeks after the monocrotaline injection. The effect of Compound A, A-NO donor, and its Poly L-Arginine Nanoformulations versus vehicle treated animals were examined. After 8 days of treatment, heart and lung tissue were harvested for histologic and molecular analyses. Compound A-NO and its poly L-arginine NP resulted in a significant reduction in PA pressures, right atrial (RA) and RV weight, and a reduction in pulmonary arteriolar medial hypertrophy, with 60-80% reduction toward full normalization of PA pressure, RA and RV weight. In contrast, Compound A without NO donor and not encapsulated into Poly L-Arginine NP resulted 20-30% reduction in PA pressure, RA and RV weight.

While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed:

1. A method for treating a subject having a vascular disorder, said method comprising administering a therapeutic effective amount of a nanoparticle to the subject to treat the disorder, wherein the vascular disorder is selected from the group consisting of sickle cell disease, an angiogenesis-mediated disorder, pulmonary hypertension, and combinations thereof, and wherein the nanoparticle comprises a poly L-arginine polymer and a Factor VIIa inhibitor conjugated to or encapsulated in the poly L-arginine polymer, wherein the Factor VIIa inhibitor is selected from the group consisting of:

Factor VIIa inhibitor I

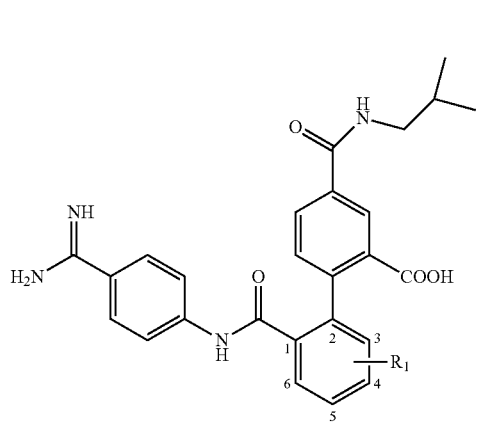

(I)

in which $R_1$ is independently selected from the group consisting of hydrogen and a NO donor at positions 3, 4, 5, and 6;

Factor VIIa inhibitor II

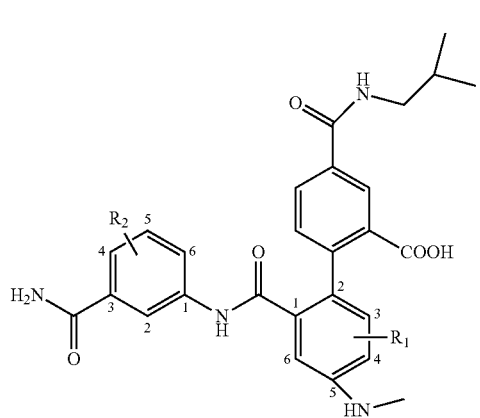

(II)

in which $R_1$ is independently selected from the group consisting of hydrogen and a NO donor at positions 3, 4, and 6 and in which $R_2$ is independently selected from the group consisting of hydrogen and a NO donor at positions 2, 4, 5, and 6, wherein for each position at which $R_2$ is independently selected as the NO donor, the NO donor is selected independently from the group consisting of $R_{11}$, $R_{12}$, $R_{13}$, $R_{14}$, $R_{15}$, $R_{16}$, $R_{17}$, $R_{18}$, and $R_{19}$;

Factor VIIa inhibitor III

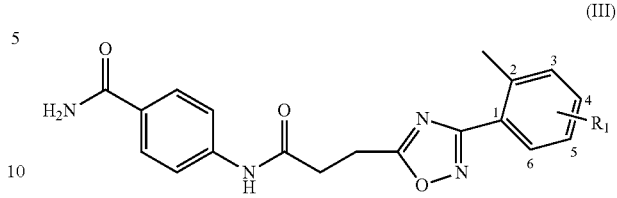

(III)

in which $R_1$ is independently selected from the group consisting of hydrogen and a NO donor at positions 3, 4, 5, and 6; and Factor VIIa inhibitor IV

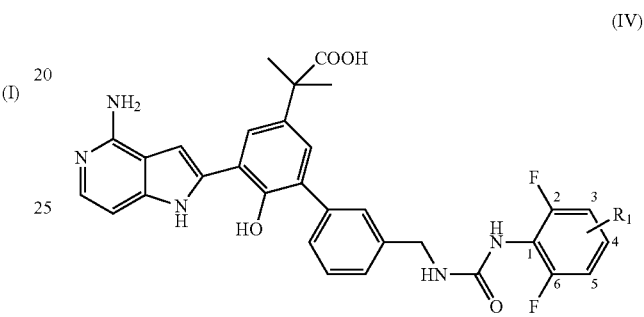

(IV)

in which $R_1$ is independently selected from the group consisting of hydrogen and a NO donor at positions 3, 4, and 5;
wherein the Factor VIIa inhibitor includes at least one NO donor, and
wherein for each position in each Factor VIIa inhibitor of Factor VIIa inhibitors I, II, III, and IV at which $R_1$ is independently selected as the NO donor, the NO donor is selected independently from the group consisting of $O=N-S-$  ($R_{11}$), $-ONO_2$  ($R_{12}$), $-CH_2ONO_2$  ($R_{13}$), $-CH_2CH_2ONO_2$  ($R_{14}$), $-C(=NOH)(CH_2)_3ONO_2$  ($R_{15}$), $-CH_2CH(ONH_2)CH_2ONO_2$  ($R_{16}$),

($R_{17}$)

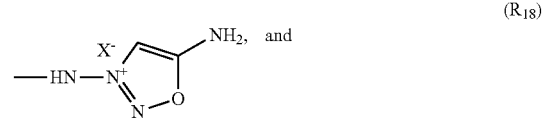

($R_{18}$)

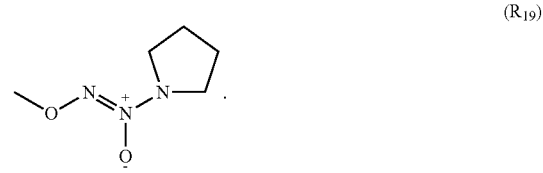

($R_{19}$)

2. The method of claim 1, wherein the Factor VIIa inhibitor is encapsulated in the poly L-arginine polymer and is not covalently bonded to the poly L-arginine polymer.

3. The method of claim 1, wherein the Factor VIIa inhibitor is conjugated to the poly L-arginine polymer by being covalently bonded to the poly L-arginine polymer.

4. The method of claim 1, wherein the poly L-arginine polymer is cross-linked with at least one substance selected from the group consisting of chitosan, poly(lactic-co-glycolic) acid (PLGA), fatty acids, bile acids, amino acids, hyaluronic acid, and combinations thereof.

5. The method of claim 1, wherein the poly L-arginine polymer is cross-linked to chitosan.

6. The method of claim 1, wherein the therapeutic effective amount is in a range of 0.1-10 mg per kilogram of body weight of the subject.

7. The method of claim 1, wherein the vascular disorder is the angiogenesis-mediated disorder.

8. The method of claim 7, wherein the angiogenesis-mediated disorder comprises breast cancer, pancreatic cancer, prostate cancer, or combinations thereof.

9. The method of claim 7, wherein the angiogenesis-mediated disorder comprises tumor angiogenesis, tumor growth, or a combination thereof.

10. The method of claim 7, wherein the angiogenesis-mediated disorder comprises an ocular angiogenesis-mediated disorder.

11. The method of claim 10, wherein the ocular angiogenesis-mediated disorder is selected from the group consisting of diabetic retinopathy and macular degeneration.

12. The method of claim 1, wherein the vascular disorder comprises pulmonary hypertension.

13. The method of claim 1, wherein the vascular disorder comprises sickle cell disease.

14. A method for treating a subject having a vascular disorder, said method comprising administering a therapeutic effective amount of a chemical structure to the subject to treat the disorder, wherein the vascular disorder is selected from the group consisting of sickle cell disease, an angiogenesis-mediated, pulmonary hypertension, and combinations thereof, and wherein the chemical structure comprises Factor VIIa inhibitor that includes at least one nitric oxide (NO) donor, wherein the Factor VIIa inhibitor is selected from the group consisting of:

Factor VIIa inhibitor I

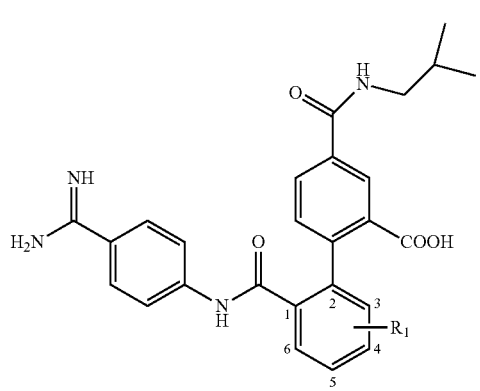

(I)

in which $R_1$ is a NO donor at positions 3, 4, 5, and 6;

Factor VIIa inhibitor II

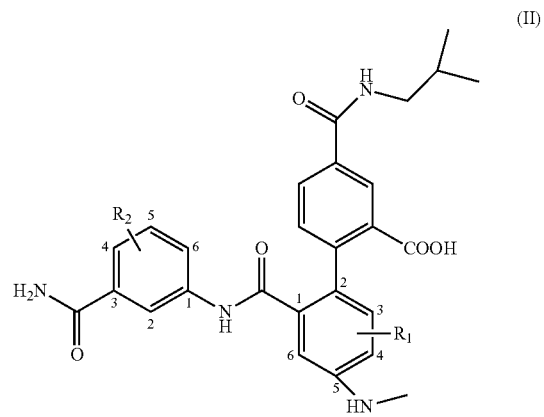

(II)

in which $R_1$ is a NO donor at position 3, 4, and 6 and in which $R_2$ is a NO donor at position 2, 4, 5, and 6,
wherein for each position of $R_2$, the NO donor is selected independently from the group consisting of $R_{11}$, $R_{12}$, $R_{13}$, $R_{14}$, $R_{15}$, $R_{16}$, $R_{17}$, $R_{18}$ and $R_{19}$;
which is Factor VIIa inhibitor III

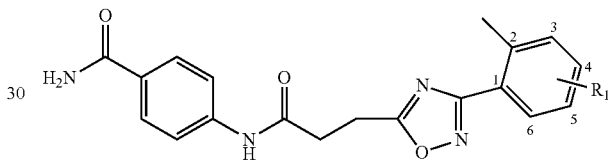

(III)

in which $R_1$ is a NO donor at positions 3, 4, 5, and 6; and
Factor VIIa inhibitor IV

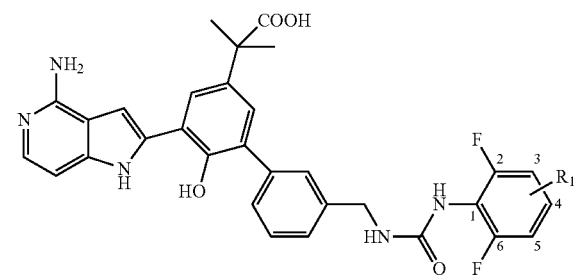

(IV)

in which $R_1$ is a NO donor at positions 3, 4, and 5;
wherein for each position in each Factor VIIa inhibitor of Factor VIIa inhibitors I, II, III, and IV at which $R_1$ exists as the NO donor, the NO donor is selected independently from the group consisting of $$O=N-S-\quad (R_{11}),$$

$$-ONO_2 \quad (R_{12}),$$

$$-CH_2ONO_2 \quad (R_{13}),$$

$$-CH_2CH_2ONO_2 \quad (R_{14}),$$

$$-C(=NOH)(CH_2)_3ONO_2 \quad (R_{15}),$$

$$-CH_2CH(ONH_2)CH_2ONO_2 \quad (R_{16}),$$

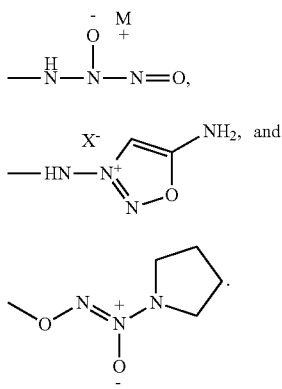

15. The method of claim 14, wherein the therapeutic effective amount is in a range of 0.1-10 mg per kilogram of body weight of the subject.

16. The method of claim 14, wherein the vascular disorder is the angiogenesis-mediated disorder.

17. The method of claim 16, wherein the angiogenesis-mediated disorder comprises breast cancer, pancreatic cancer, prostate cancer, or combinations thereof.

18. The method of claim 16, wherein the angiogenesis-mediated disorder comprises tumor angiogenesis, tumor growth, or a combination thereof.

19. The method of claim 16, wherein the angiogenesis-mediated disorder comprises an ocular angiogenesis-mediated disorder.

20. The method of claim 19, wherein the ocular angiogenesis-mediated disorder is selected from the group consisting of diabetic retinopathy and macular degeneration.

21. The method of claim 14, wherein the vascular disorder comprises pulmonary hypertension.

22. The method of claim 14, wherein the vascular disorder comprises sickle cell disease.

* * * * *

UNITED STATES PATENT AND TRADEMARK OFFICE
CERTIFICATE OF CORRECTION

Page 1 of 1

PATENT NO. : 8,980,823 B2
APPLICATION NO. : 13/935665
DATED : March 17, 2015
INVENTOR(S) : Mousa It is certified that error appears in the above-identified patent and that said Letters Patent is hereby corrected as shown below:

In the specification,
Column 17, Line 26, change "KB" to --$_K$B--.

Column 18, Line 54, delete "µA" and add --µl--.

Column 18, Line 60, delete "µA" and add --µl--.

In the claims,
Column 31, Line 7, delete "and" after the structural formula.

Signed and Sealed this
Eighth Day of December, 2015

Michelle K. Lee
*Director of the United States Patent and Trademark Office*